US012788044B2

(12) United States Patent
Godard et al.

(10) Patent No.: US 12,788,044 B2
(45) Date of Patent: Nov. 10, 2026

(54) EXTRACTS FROM FAST GROWING MICROBES

(71) Applicant: MICROHARVEST GMBH, Hamburg (DE)

(72) Inventors: Thibault Godard, Hamburg (DE); Mazen Rizk, Hamburg (DE)

(73) Assignee: Micro Harvest GmbH, Hamburg (DE)

( * ) Notice: Subject to any disclaimer, the term of this patent is extended or adjusted under 35 U.S.C. 154(b) by 192 days.

(21) Appl. No.: 18/572,725

(22) PCT Filed: Jun. 21, 2022

(86) PCT No.: PCT/EP2022/066931

§ 371 (c)(1),
(2) Date: Dec. 20, 2023

(87) PCT Pub. No.: WO2022/268842

PCT Pub. Date: Dec. 29, 2022

(65) Prior Publication Data

US 2024/0284954 A1 Aug. 29, 2024

(30) Foreign Application Priority Data

Jun. 21, 2021 (EP) .................................... 21180714

(51) Int. Cl.
*A23L 33/13* (2016.01)
*A23J 1/00* (2006.01)
(Continued)

(52) U.S. Cl.
CPC ............... *A23L 33/13* (2016.08); *A23J 1/008* (2013.01); *A23K 10/12* (2016.05); *A23K 20/147* (2016.05);
(Continued)

(58) Field of Classification Search
CPC .... A23K 20/147; A23K 20/153; A23K 10/12; A23L 33/13; A23L 33/18; A23L 33/175; C12N 1/205; A23J 1/008
See application file for complete search history.

(56) References Cited

U.S. PATENT DOCUMENTS

2003/0044951 A1 * 3/2003 Sporleder ................ C12N 1/00 426/18
2017/0037081 A1 2/2017 Xu et al.

FOREIGN PATENT DOCUMENTS

CN 101155929 A 4/2008
CN 102471791 A 5/2012
(Continued)

OTHER PUBLICATIONS

Matassa et al. "Microbial protein: future sustainable food supply route with low environmental footprint" in Microbial Biotechnology (2016) 9(5), 568-575. (Year: 2016).*
(Continued)

*Primary Examiner* — Blessing M Fubara
(74) *Attorney, Agent, or Firm* — Womble Bond Dickinson (US) LLP

(57) ABSTRACT

The present invention relates to the method for production of a composition comprising at least 15% nucleotides, preferably at least 18% nucleotides, more preferably at least 22% nucleotides and at least 40% amino acids and peptides, and to a composition comprising at least 15% nucleotides, preferably at least 18% nucleotides, more preferably at least 22% nucleotides and at least 40% amino acids and peptides obtainable according to the said method. The method of the present invention involves obtaining the biomass by cultivating at least one microorganism strain(s) characterized by a growth rate in the process of at least 0.85 h-1. The composition of the present invention is particularly useful in the production of animal feed, pet food, food products,
(Continued)

fermentation medium or supplement, nutraceuticals, pharmaceuticals, diagnostics, RNA or DNA, or flavour enhancers.

14 Claims, 1 Drawing Sheet

(51) Int. Cl.

| | |
|---|---|
| ***A23K 10/12*** | (2016.01) |
| ***A23K 20/147*** | (2016.01) |
| ***A23K 20/153*** | (2016.01) |
| ***A23L 33/175*** | (2016.01) |
| ***A23L 33/18*** | (2016.01) |
| ***C12N 1/205*** | (2026.01) |

(52) U.S. Cl.
CPC .......... *A23K 20/153* (2016.05); *A23L 33/175* (2016.08); *A23L 33/18* (2016.08); *C12N 1/205* (2021.05)

(56) References Cited

FOREIGN PATENT DOCUMENTS

| | | | | |
|---|---|---|---|---|
| CN | 106721247 A | 5/2017 | | |
| EP | 1587947 B1 * | 1/2010 | .............. | C12P 19/30 |
| JP | 2002-101846 A | 4/2002 | | |
| JP | 2006-129834 A | 5/2006 | | |
| JP | 2007-521805 A | 8/2007 | | |

OTHER PUBLICATIONS

Des Soye et al. "Establishing a High-Yielding Cell-Free Protein Synthesis Platform Derived from Vibrio natriegens" in Synthetic Biology, 2018, 7:2245-2255. (Year: 2018).*

Des Soye et al., "Establishing a High-Yielding Cell-Free Protein Synthesis Platform Derived from *Vibrio natriegens*," ACS Synth. Biol., 2018, 7:2245-2255.

Failmezger et al., "Cell-Free Protein Synthesis From Fast-Growing *Vibrio natriegens*," Frontiers in Microbiology, 2018, vol. 9, Article 1146, 10 pp.

Ritala et al., "Single Cell Protein—State-of-the-Art, Industrial Landscape and Patents 2021-2016," Frontiers in Microbiology, 2017, vol. 8, Article 2009, 18 pp.

Wiegand et al., "Cell-free Protein Expression Using the Rapidly Growing Bacterium *Vibrio natriegens*," JOVE, 2019, 145:e59495, 14 pp.

International Search Report and Written Opinion issued Sep. 22, 2022, in PCT application No. PCT/EP2022/066931.

Office Action issued Jan. 7, 2026, in Chinese Patent Application No. 202280043961.3.

Weiwei, Wang, Microbial Physiology, 1st Edition, Dec. 31, 2008, 6 pp.

Office Action issued Jul. 21, 2026, in Chinese Patent Application No. 202280043961.3.

Office Action issued Jun. 30, 2026, in Japanese Patent Application No. 2023-578792.

* cited by examiner

A.
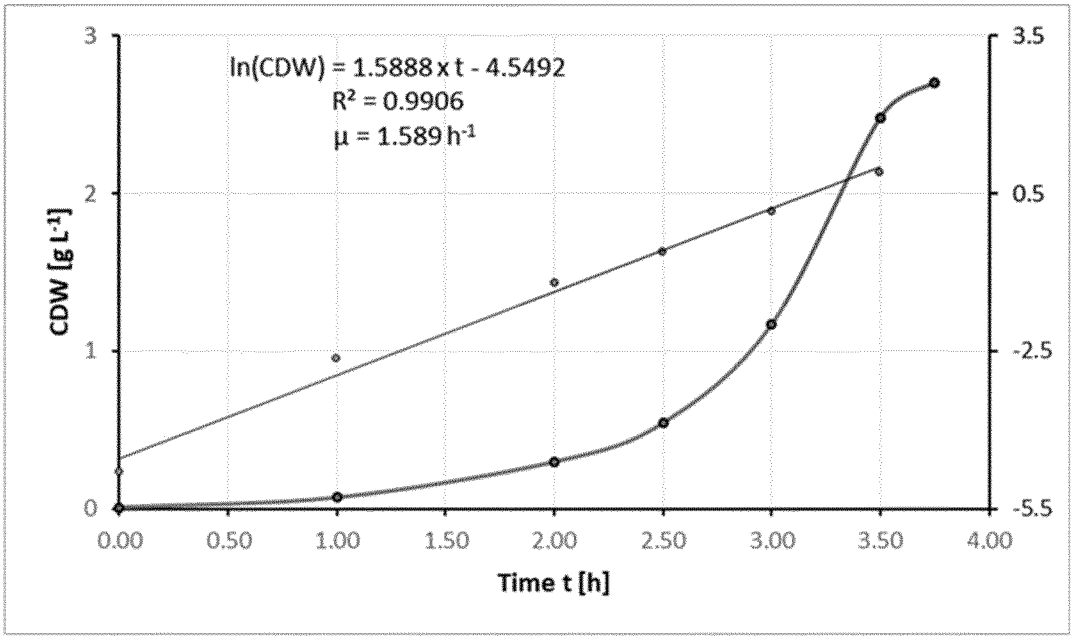
B.
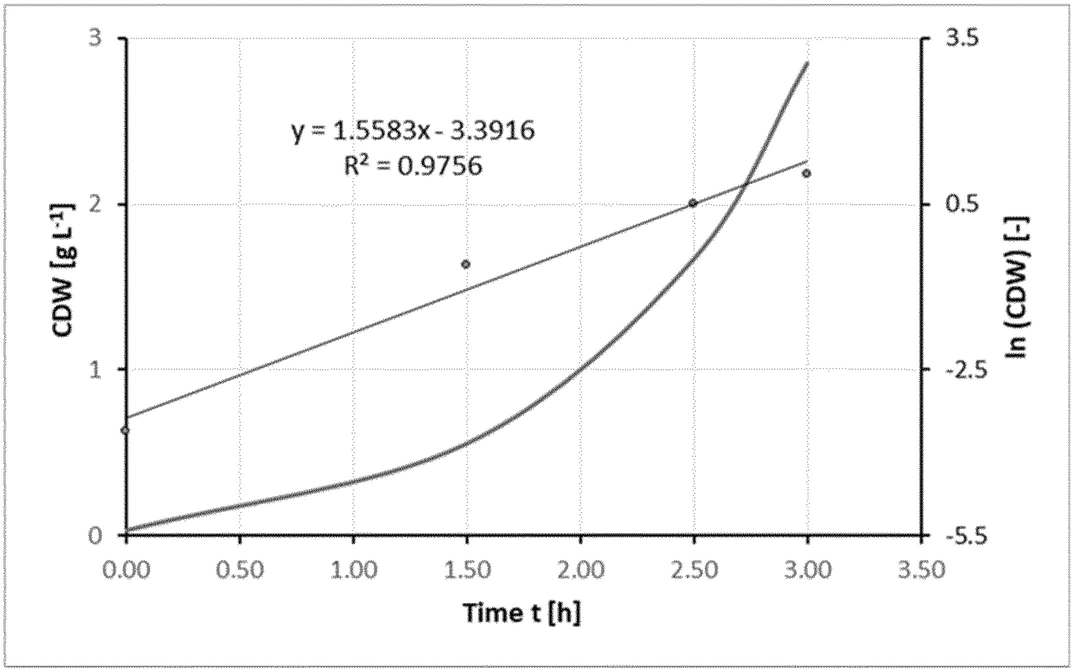

EXTRACTS FROM FAST GROWING MICROBES

CROSS REFERENCE TO RELATED APPLICATIONS

This application is a national stage filing under 35 U.S.C. 371 of PCT/EP2022/066931 filed Jun. 21, 2022, which International Application was published by the International Bureau in English on Dec. 29, 2022, and application claims priority from European Patent Application No. 21180714.4, filed Jun. 21, 2021, which applications are hereby incorporated in their entirety by reference in this application.

FIELD OF THE INVENTION

The present invention relates to the method for production of a composition comprising at least 15% nucleotides, preferably at least 18% nucleotides, more preferably at least 22% nucleotides and at least 40% amino acids and peptides, and to a composition comprising at least 15% nucleotides, preferably at least 18% nucleotides, more preferably at least 22% nucleotides and at least 40% amino acids and peptides obtainable according to the said method. The method of the present invention involves obtaining the biomass by cultivating at least one microorganism strain(s) characterized by a growth rate in the process of at least 0.85 $h^{-1}$. The composition of the present invention is particularly useful in the production of animal feed, pet food, food products, fermentation medium or supplement, cosmetics, pharmaceuticals, diagnostic agents, DNA or RNA, nutraceuticals or flavour enhancers.

BACKGROUND

Although bacteria are widely used in food production, e.g. lactic acid bacteria in fermented dairy products like yoghurt and cheese or sausages, they are currently only starting to be used as direct food ingredients for human or animal consumption. However, changing this would have a significant positive environmental impact as fermenter-grown microbe protein could replace cropland-grown protein like soybeans or harvested ones like fish meal, thereby reducing water, fertilizer and pesticide consumption as well as green-house gas emissions. It could also lead to a reduced use of land. Next to protein as essential feed and food ingredients, bacteria, in particular the fast-growing bacteria contain a surprisingly high amounts of nucleic acids. Nucleic acids can be converted to nucleotides in high concentration, which in turn can be used in food and feed production, and in related applications. Nucleotides have been shown to be semi-essential feed ingredients. In particular, under stress conditions, the organism's capability of producing the nucleotides is limited and therefore external sources of this nutrient are necessary. Nucleotides positively affect immune system modulation and feed uptake. Further, nucleotides can, at least in part, replace antibiotics in feed applications. More specifically, nucleotides can improve the effectiveness of antimicrobial solutions that are known to the skilled person as being less effective than antibiotics.

Moreover, 5'-ribonucleotides, and more specifically 5'-inosine monophosphate (5'-IMP) and 5'-guanine monophosphate (5'-GMP), have been shown to improve taste of feed and food products alone and when combined with glutamate by providing them with a stronger umami note. It is noted that improved taste of feed may play a role in feed uptake, i.e. increase feed efficacy and reduce costs. A stronger umami note either occurs naturally in a number of foods (e.g. ripened cheese, meat, soy sauce or miso paste) or when nucleotides and glutamate are added to enhance the umami taste (e.g. in savoury products like soups and sauces). This has been promoted for decades in yeast extracts and made them a food additive of choice when included in savoury products. In humans, nucleotides are most of the time de novo synthesized in energy consuming reaction cascades and take part in central metabolic functions, such as RNA/DNA biosynthesis required during cell division or protein synthesis, metabolic regulation and cell signalling. Supplementation of dietary nucleotides has been shown to be beneficial for the intestinal development and gastro-intestinal function and several other prebiotic effects have been documented. Of note, more recently, the use of 5'-ribonucleotides have also shown a promising potential for sugar and salt reduction. 5'-Ribonucleotides can also be used in the preparation of sport drinks for improved recovery after workout.

One of the drawbacks of existing additives comprising nucleotides is that the concentration of nucleotides is limited, requiring in some applications adding of larger amounts, that can lead to off-flavours, i.e. undesired and/or unpleasant taste, which is not due to nucleotides but may be due to their components beyond nucleotides, or imposing cost-intensive processing step to obtain concentrated nucleotides solution.

The granted patent EP 1 587 947 relates to a composition comprising at least 55% w/w (on sodium chloride free dry matter weight) of 5'-ribonucleotides and a process of production thereof.

Patent application WO 2016/161549 discloses a method for producing an aerobic single cell protein by using an autolysis process.

SUMMARY

The present invention relates to the production of environmentally friendly extracts containing high concentrations of proteins and nucleotides, in particular nucleotides, especially 5'-ribonucleotides, that are useful as additives to food products, animal feed and fermentation media. The said extracts are produced from fast-growing bacteria grown in fermenters using conventional growth media or preferably, aqueous media or extracts obtained from agro-industrial sidestreams. The present invention also relates to the specific use of bacteria with extremely high nucleic acid content (up to 40%), which brings a significant advantage for the production of extracts rich in 5'-ribonucleotides compared to classical yeast or algae extracts or currently available bacterial extracts. The presented invention furthermore focuses on the use of bacteria with a growth rate of at least 0.85 $h^{-1}$, preferably bigger than 1.1 $h^{-1}$, obtained from fermentation processes known in the art but also using a continuous process at a dilution rate D [$h^{-1}$] higher than any currently known processes to avoid contamination by other microorganisms and further increase both process and cost efficiency. Compared to extracts from other bacteria or sources like algae or yeast they appear to be beneficial in applications like taste enhancement, sugar or salt reduction, antibiotic replacement for feed or high-performance fermentation additives. Of particular interest is the unique composition and growth speed of the microorganisms used that enable low production costs and significantly reduce the possibility of contamination by other microorganisms.

It was an objective technical problem of the present invention to provide improved means and methods for production of a composition with high nucleotide content.

The problem described herein is solved by the embodiments described in the following and as characterized in the claims.

The invention will be summarized in the following aspects.

In a first aspect, the present invention relates to a method for the production of a composition comprising at least 15% nucleotides, preferably at least 18% nucleotides, more preferably at least 22% nucleotides and at least 40% amino acids and peptides, the method comprising the steps of: (a) providing biomass by cultivating at least one microorganism strain(s) characterized by a growth rate in the process of at least 0.85 $h^{-1}$, (b) lysing the cells present in the biomass of step (a), and (c) converting the nucleic acid present in the lysate of step (b) to nucleotides and optionally converting protein present in the lysate of (b) to amino acids and peptides, wherein % are understood as w/w % of dry mass excluding NaCl.

In a particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) of step (a) is/are characterized by a growth rate in process of at least 1.1 $h^{-1}$, preferably at least 1.2 $h^{-1}$, more preferably at least 1.4 $h^{-1}$.

In a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) of step (a) is/are characterized by a nucleic acid content of at least 15%, preferably at least 20% nucleotides, more preferably at least 22%, more preferably of at least 25%, even more preferably at least 28%.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) of step (a) comprises a bacterial strain, preferably a halophile or a thermophile, preferably wherein a bacterial strain is characterized by a genomic G/C content of at least 40%, more preferably of at least 45%, even more preferably of at least 50%, most preferably of at least 55%.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) of step (a) comprises a microorganism that is a vitamin B12 autotroph.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (a) is performed as a continuous process with a dilution rate of at least 0.85 $h^{-1}$, preferably of at least 1.1 $h^{-1}$, more preferably at least 1.2 $h^{-1}$, even more preferably at least 1.4 $h^{-1}$, wherein the growth rate in process of each of the at least one microorganism strain(s) of step (a) is limited by the dilution rate, and optionally wherein the at least one microorganism strain(s) is cultivated under non-sterile conditions.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) of step (a) are two microorganism strains, preferably two bacterial strains, further preferably wherein at least one bacterial strain is a vitamin B12 autotroph.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) comprises a microorganism strain selected from *Vibrio* spp, in particular *Vibrio natriegens, Geobacillus* spp, in particular *Geobacillus* LC300, and *Bacillus* spp, in particular *Bacillus megaterium.*

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) comprises a microorganism able to synthesize omega-3 fatty acids.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein the at least one microorganism strain(s) comprises a genetically modified microorganism.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (b) involves heat pre-treatment performed at a temperature of between 70° C. and 180° C. and/or for a time of between 10 minutes and 360 minutes, followed by enzymatic treatment with protease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (b) is performed by mechanical homogenization, and optionally involves heat pre-treatment performed at a temperature of between 70° C. and 180° C. and/or for a time of between 10 minutes and 360 minutes.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (c) involves enzymatic treatment with nuclease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (c) further comprises enzymatic treatment with deaminase(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (c) further comprises enzymatic treatment with protease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.

In a further aspect, the present invention relates to a composition comprising at least 15% nucleotides, preferably at least 18% nucleotides, more preferably at least 22% nucleotides and at least 40% protein and/or amino acids and peptides, obtainable according to the method for the production of a composition comprising at least 15% nucleotides, preferably at least 18% nucleotides, more preferably at least 22% nucleotides and at least 40% amino acids and peptides of the present invention.

In a particular aspect, the composition comprising at least 15% nucleotides, preferably at least 18% nucleotides, more preferably at least 22% nucleotides and at least 40% protein and/or amino acids and peptides of the present invention relates to an embodiment, wherein the composition is characterized in IMP/GMP content of at least 11%, preferably at least 13%, even more preferably at least 15%, most preferably at least 17%.

In a further particular aspect, the composition comprising at least 15% nucleotides, preferably at least 18% nucleotides, more preferably at least 22% nucleotides and at least 40% protein and/or amino acids and peptides of the present invention relates to an embodiment, wherein the composition further comprises glutamate content of at least 6% w/w, preferably of at least 8% w/w, more preferably of at least 10% w/w, even more preferably of at least 12% w/w, even more preferably of at least 14% w/w, most preferably of at least 16% w/w.

In a further aspect, the present invention relates to use of the composition comprising at least 15% nucleotides, preferably at least 18% nucleotides, more preferably at least 22% nucleotides and at least 40% protein and/or amino acids and peptides of the present invention in the production of animal feed, pet food, fermentation medium or supplement, food products, nutraceuticals, pharmaceuticals, diagnostics agents, DNA or RNA, or flavour enhancers.

In again a further aspect, the present invention relates to animal feed, pet food, food product, fermentation medium or supplement, nutraceutical or flavour enhancer comprising the composition comprising at least 15% nucleotides, preferably at least 18% nucleotides, more preferably at least 22% nucleotides and at least 40% protein and/or amino acids and peptides of the present invention.

In a further aspect, the present invention relates to use of the composition comprising at least 15% nucleotides, preferably at least 18% nucleotides, more preferably at least 22% nucleotides and at least 40% protein and/or amino acids and peptides of the present invention as a monosodium glutamate replacement or as/in an antibiotic replacement.

In again a further aspect, the present invention relates to a biomass obtainable in step (a) of the method according for the production of a composition comprising at least 15% nucleotides, preferably at least 18% nucleotides, more preferably at least 22% nucleotides and at least 40% amino acids and peptides of the present invention.

In a particular aspect, the biomass of the present invention relates to an embodiment, wherein the glutamate content is at least 5% w/w, preferably at least 6% w/w, more preferably at least 7% w/w, even more preferably at least 8% w/w, even more preferably at least 9% w/w, even more preferably at least 10% w/w, most preferably at least 12%. Further, the biomass of the present invention preferably has the nucleic acid content of at least 15%, preferably at least 20%, more preferably of at least 22% w/w, more preferably of at least 25% w/w, even more preferably at least 28% w/w.

In a further aspect, the present invention relates to a single cell protein comprising the biomass of the present invention.

In a particular aspect, the single cell protein of the present invention relates to an embodiment, wherein the single cell protein that has further undergone heat treatment.

In a further aspect, the present invention relates to use of single cell protein of the present invention in the production of animal feed, pet food or food products, preferably animal feed.

In again a further aspect, the present invention relates to a cell lysate obtainable in step (b) of the method for the production of a composition comprising at least 15% nucleotides, preferably at least 18% nucleotides, more preferably at least 22% nucleotides and at least 40% amino acids and peptides of the present invention.

In again a further aspect, the present invention relates to a composition comprising nucleotides obtainable in a process comprising the step of separation, preferably by ultrafiltration, of the cell lysate of the present invention.

In again a further aspect, the present invention relates to a composition comprising amino acids and peptides obtainable in a process comprising the step of separation, preferably by ultrafiltration, of the cell lysate of the present invention.

In again a further aspect, the present invention relates to use of the composition comprising nucleotides obtainable in a process comprising the step of separation, preferably by ultrafiltration, of the cell lysate of the present invention or the composition comprising amino acids and peptides obtainable by separation, preferably by ultrafiltration, of the cell lysate of the present invention in the production of animal feed, pet food, food products, fermentation medium or supplement, nutraceuticals, diagnostics agents, pharmaceuticals, DNA or RNA, or flavour enhancers.

In again a further aspect, the present invention relates to animal feed, pet food, food product, fermentation medium or supplement, nutraceutical, diagnostics agents, pharmaceuticals, DNA or RNA. or flavour enhancer comprising the composition comprising nucleotides obtainable in a process comprising the step of separation, preferably by ultrafiltration, of the cell lysate of the present invention or the composition comprising amino acids and peptides obtainable by separation, preferably by ultrafiltration, of the cell lysate of the present invention.

Definitions

The growth rate in the process is defined herein as the growth rate achievable under the fermentation conditions. In other words, for a microorganism to be suitable for the use within the method of the present invention it must be possible to cultivate it with the growth rate as defined herein in the fermentation conditions, in particular on a specific growth medium. The growth rate in the process as defined herein refers to a growth rate of a particular microorganism, unless indicated otherwise. In the case of co-cultivation of more than one microorganism, the growth rate may refer to a combined growth rate of all the microorganism in the culture, and describe the increase in combined biomass over time.

As apparent to the skilled person, the growth rate in the process is preferably determined by plotting the ln (natural logarithm) of biomass amount as a function of time and using a linear regression to calculate the slope in the linear range that corresponds to the exponential growth phase.

The growth rate in the process may also be referred to as $\mu$ [$h^{-1}$].

A dilution rate D [$h^{-1}$] of a particular culture setup, in particular in a culture comprising liquid medium, as understood herein is defined as the flow of the medium (inflow of fresh medium which equals outflow of culture) per unit of time (preferably hour), divided by the volume of culture in the reactor.

Omega-3 fatty acids as understood herein are polyunsaturated fatty acids characterized by the presence of a double bond three atoms away from the terminal methyl group in their chemical structure. In particular, the term encompasses alpha-linoleic acid, eicosapentaenoin acid and docosahexaenoic acid.

Nucleic acids as understood herein include deoxyribonucleic acid (DNA) and/or ribonucleic acid (RNA), also understood as polydeoxyribonucleotides and/or polyribonucleotides, without particular limitation on size of the polymers. It is noted that nucleic acids are formed of nucleotides.

Nucleotides as understood herein refer to deoxyribonucleotides and ribonucleotides that are monomers which upon polymerization form polydeoxyribonucleotides and/or polyribonucleotides, respectively. It is noted that the term also encompasses modified nucleotides, for example IMP which comprises inosine base. Preferably, when referring to a nucleotide content of a composition, a reference is made to nucleotides, nucleosides and nucleobases (a pyrimidine or a purine) content of the composition, even more preferably a reference is made to nucleotides and nucleosides content of the composition. Accordingly, for example, a composition comprising at least 22% nucleotides wherein % are understood as w/w % of dry mass excluding NaCl, is preferably understood to comprise at least 22% (understood as w/w % of dry mass excluding NaCl) of nucleotides, nucleosides and nucleobases, more preferably it is understood to comprise at least 22% (understood as w/w % of dry mass excluding NaCl) of nucleotides and nucleosides, i.e. preferably in total nucleotides, nucleosides and nucleobases constitute at least 22% of the composition, wherein % is understood as w/w % of dry mass excluding NaCl, more preferably in total nucleotides and nucleosides constitute at least 22% of the composition, wherein % is understood as w/w % of dry mass excluding NaCl.

Nucleosides are known to the skilled person as nucleotides lacking the phosphate moiety.

Nucleobases are understood herein preferably as including pyrimidine bases and purine bases, more preferably nucleobases are adenine, cytosine, guanine, thymine and uracil.

The term "protein" or "proteins" as used herein covers proteins, peptides and polypeptides, wherein said proteins, peptides or polypeptides may or may not have been post-translationally modified. Post-translational modification may for example be phosphorylation, methylation, glycosylation. The term "protein" is preferably used in reference to a fraction or a composition comprising proteins, as defined herein. Upon enzymatic treatment with protease(s), that is enzymes capable of catalyzing the hydrolysis of peptide bonds, peptide bonds in proteins are hydrolyzed and larger polypeptides are turned into smaller polypeptides and/or amino acids. Thus, the term "amino acids and peptides" shall refer to a composition comprising proteins, peptides (which may be referred to as polypeptides or oligopeptides) and amino acids, which is preferably understood herein as a product of protease treatment of "proteins".

BRIEF DESCRIPTION OF FIGURES

FIG. 1: Growth curves obtained for the growth of *Vibrio natriegens* on A. molasses and B. glucose. CDW herein refers to the cell dried weight. Linear regression allowing for calculating the growth rate in the process, presented as $\mu$, is shown.

DETAILED DESCRIPTION OF THE INVENTION

The means and methods of the invention will be described in the following. It is to be understood that all possible combinations of the features as described herein are also envisaged.

In a first aspect, the present invention relates to a method for the production of a composition comprising at least 15% nucleotides, preferably at least 18% nucleotides, more preferably at least 22% nucleotides and at least 40% amino acids and peptides. As preferably understood herein, the reference to nucleotides may also optionally encompass nucleosides and nucleobases (a pyridine or a purine), even more preferably the reference to nucleotides may encompass nucleotides and nucleosides. As understood herein, the reference "40% amino acids and peptides" may also optionally encompass proteins, as defined herein. Herein, the composition is understood as referring to dry mass (upon removal of water), further excluding sodium chloride content (NaCl). As understood herein, the "%" refers to a weight/weight ratio expressed as percentage (commonly referred to as w/w %). The composition (which herein may also be referred to as an extract of the present invention) as referred to herein comprises at least 15% nucleotides, preferably at least 18% nucleotides, more preferably at least 22% nucleotides, even more preferably at least 25% nucleotides, even more preferably at least 28% nucleotides, and at least 40% amino acids and peptides, preferably at least 45% amino acids and peptides, most preferably at least 50% amino acids and peptides. As understood herein, the composition of the present invention as defined herein is obtainable according to the method of the present invention.

The method of the present invention comprises the steps of: (a) providing biomass by cultivating at least one microorganism strain(s) characterized by a growth rate in the process of at least 0.85 $h^{-1}$, (b) lysing the cells present in the biomass of step (a), and (c) converting the nucleic acid present in the lysate of step (b) to nucleotides and optionally converting protein present in the lysate of (b) to amino acids and peptides, The first step of the method of the present invention (a) is providing biomass by cultivating at least one microorganism strain(s) characterized by a growth rate in the process of at least 0.85 $h^{-1}$. Preferably, fast-growing bacterial strains (the growth rate in the process (also referred to as the growth rate) is >0.9 $h^{-1}$) are used within the method of the present invention. Preferably, the at least one microorganism strain(s) of step (a) is/are characterized by a growth rate in process of at least 1.1 $h^{-1}$, preferably at least 1.2 $h^{-1}$, more preferably at least 1.4 $h^{-1}$. Also encompassed by the present invention is an embodiment, wherein the at least one microorganism strain(s) of step (a) is/are characterized by a growth rate in process of at least 2 $h^{-1}$, at least 3 $h^{-1}$, or of at least 4 $h^{-1}$. The growth rate as understood herein, unless stated otherwise, is the growth rate in the process, as defined herein. As it is apparent to the skilled person, the growth rate in the process may depend on the growth medium, and be different for minimal medium and rich medium, as understood to the skilled person.

The microorganisms that grow fast, as defined herein, commonly are characterized by the high nucleic acid content, in comparison with microorganisms that grow relatively slower. The present inventors have surprisingly found that by using the microorganism with high nucleic acid content an expensive step of separation of nucleic acids and proteins can be omitted, thus simplifying the production of the extract and reducing its cost. As known to the skilled person, the level of at least 22% nucleotides has to date been achievable only by including further nucleic acid separation and/or concentration steps following the cell lysis, as demonstrated in the prior art, for example when using yeast extracts. As further known to the skilled person, the level of at least 15% nucleotides has to date been achievable only by including further nucleic acid separation and/or concentration steps following the cell lysis, as demonstrated in the prior art, for example when using yeast extracts. Thus preferably, in the method of the present invention the at least one microorganism strain(s) of step (a) is/are characterized by a nucleic acid content of preferably at least 15%, more preferably at least 20%, even more preferably at least 22%, even more preferably of at least 25%, even more preferably at least 28%. Preferably, in the method of the present invention the at least one microorganism strain(s) of step (a) is/are characterized by a nucleic acid content of at least 22%, preferably of at least 25%, even more preferably at least 28%. For yeast extracts, the nucleic acid content in yeast is lower, typically about 10% and has to be separated beforehand and further processed to reach the nucleotides content in the final extract comparable to that reachable according to the methods of the present invention.

Suitable examples include *Vibrio natriegens, Geobacillus* and *Bacillus* strains. Thus preferably, in the method of the present invention the at least one microorganism strain(s) comprises a microorganism strain selected from *Vibrio* spp, in particular *Vibrio natriegens, Geobacillus* spp, in particular *Geobacillus* LC300, and *Bacillus* spp, in particular *Bacillus megaterium*. Preferably, the at least one microorganism strain is selected from *Vibrio* sbb, in particular *Vibrio natriegens*. Further suitable examples of *Geobacillus* spp. may include *Geobacillus uralicus*, and *Geobacillus stearothermophilus*. Further suitable examples of *Bacillus* spp may include *Bacillus licheniformis, Bacillus coagulans* and *Bacillus stearothermophilus*.

Preferably, the at least one microorganism strain of step (a) as defined herein comprises a bacterial strain. The bacterial strain can be an extremophile. Preferably, the bacterial strain is a halophile or a thermophile. Halophiles are defined herein as organisms, herein in particular microorganisms, that require high salt, in particular NaCl, concentration for growth and survival. Slight halophiles preferably grow in the NaCl concentration of at least 0.3 M and not exceeding 0.8 M. Moderate halophiles preferably grow in the NaCl concentration of at least 0.8 M and not exceeding 3.4 M. Extreme halophiles preferably grow in the NaCl concentration of at least 3.4 M and not exceeding 5.1 M. In certain embodiments, the halophile as described herein is an extreme halophile. It is further noted that certain organisms, in particular microorganisms, do not require high salt concentration for survival, but can tolerate such conditions. Such microorganism can also be referred to as halotolerant organism. The at least one microorganism strain of the present invention may comprise a halotolerant organism. It is noted that in the embodiments wherein the at least one microorganism of step (a) is a halophile or a halotolerant organism, sea water could be used for preparation of the medium for cultivation step (a) instead of groundwater, tap water or distilled water. In certain embodiments said halophile or halotolerant organism could grow faster than other microbes and hence overgrow them. Thus, in certain embodiments the sea water could be used without further sterilization, filtration and/or pasteurization. The bacterial strain as defined herein may be a thermophile. Thermophile is understood herein as an organism, in particular a microorganism that preferably grows at elevated temperature, that means preferably between 41° C. and 122° C. It is noted that the use of halophile and/or thermophile microorganisms is advantageous because it significantly reduces the risk of contamination by other microorganisms.

The bacterial strains that are extremophiles, in particular halophiles or thermophiles, are typically characterized by high genomic G/C content. Genomic G/C content is herein defined as the ratio of amount G and C nucleotides in the DNA of said organism to the total amount of nucleobases in the DNA of said organism. As Understood herein, a bacterial strain of the present invention, preferably a halophile or a thermophile, is characterized by a genomic G/C content of at least 40%, more preferably of at least 45%, even more preferably of at least 50%, most preferably of at least 55%. As pointed out above, G is the only natural nucleobase that significantly contributes to savoury taste enhancement properties, in particular stronger umami note. Therefore, increased G/C content, directly translatable to an increased presence of 5'-guanine monophosphate (5'-GMP) in the extract of the present invention, allows for obtaining a stronger umami note in the extracts of the present invention. It further leads to the cost reduction, as less enzyme, in particular deaminase, is required for obtaining a stronger umami note in the extracts of the present invention.

The at least one microorganism strain(s) of the present invention may comprise a microorganism that is a vitamin B12 autotroph. Presence of vitamin B12 in food is required and in particular it is desirable in the case of vegan diet and/or products that are suitable for vegan diet. Preferably the microorganism that is a vitamin B12 autotroph is *Bacillus megaterium*. It is noted that the vitamin B12 autotroph would be considered interesting as a natural source of vitamin B12 for the organic farming industry.

It is herein noted that within the scope of the present invention the at least one microorganism strain(s) does not necessarily need to be limited to a single microorganism strain. Within the scope of the method of the present invention, the at least one microorganism strain(s) may be two, three, four or more strains. In certain preferred embodiment, the at least one microorganism strain(s) of step (a) are two microorganism strains, preferably two bacterial strains. In certain preferred embodiments wherein the at least one microorganism strain(s) is two bacterial strains, at least one bacterial strain is a vitamin B12 autotroph, preferably *Bacillus megaterium.*

In certain embodiments of the present invention the at least one microorganism strain(s) preferably comprises a genetically modified microorganism. Said genetically modified organism is not particularly limited and may include genetic modification to improve growth rate, biomass yield, and/or induce production of certain chemical substances. In certain embodiments of the present invention the at least one microorganism strain(s) comprises a microorganism able to synthesize omega-3 fatty acids.

According to the present invention, biomass of the present invention is obtainable by cultivating at least one microorganism strain(s) characterized by a growth rate in the process of at least 0.85 $h^{-1}$. As understood herein, the at least one microorganism strain(s) is to be cultivated on a substrate. The skilled person would be capable of selecting, adjusting and/or applying particular medium/media to the at least one microorganism strain(s) as used in the invention. The substrate used can be any commercial medium including carbon and nitrogen source as well as trace elements and vitamins. Preferably, the substrate can be one or several side-streams from the industry, either extracted by thermal and/or enzymatic methods or directly used for fermentation and containing either proteins, C5 sugars, C6 sugars or a combination of those. The one or several sidestream(s) can then be supplemented with other compounds to obtain a suitable growth medium (e.g. additional sugars as carbon source or nitrogen sources such as yeast extracts as well as vitamins and trace elements). Medium is preferably sterilized before inoculation of fermenters as known to the skilled person familiar with industrial fermentation process.

As known to the skilled person, the fermentation may be performed as a batch process, fed-batch process or (semi) continuous process.

The batch processes are characterized by lack of inflow of material into the fermentation vessel. In a batch process, all nutrients are provided at the beginning of the cultivation, without adding any more in the subsequent bioprocess. During the entire bioprocess, no additional nutrients are added with the exception of gases, acids and bases. In certain embodiments, an antifoaming agent may also be added. The bioprocess then lasts until one of the nutrients required for growth becomes limiting. This strategy is suitable for rapid experiments such as strain characterization or the optimization of nutrient medium. The disadvantage of this convenient method is that the biomass and product yields are limited. Since the carbon source and/or oxygen transfer are usually the limiting factor, the microorganisms are not in the exponential growth phase for a long time. After the end of a bioprocess run in batch mode, only the biomass or medium is harvested and appropriately processed to obtain the desired product. From the bioreactor point of view, the process is repeatedly interrupted by cleaning and, when needed, sterilization steps, and the biomass is only produced in stages.

In the fed batch process, substrate, nutrients and other substances may be added (preferably, in a form of a concentrated solution) into the fermentation vessel, to extend the possible culture time or increase the yield, among others. The advantage of feeding during cultivation is that it allows to achieve higher product quantities overall. Under specific growth conditions, the microorganisms and/or cells constantly double and therefore follow an exponential growth curve. Therefore, in certain embodiments the feed rate may be increased exponentially as well. Generally, the substrate is pumped from the supply bottle (or a feed tank) into the culture vessel, for example through a silicone tube (or a sterilizable piping). The user can either manually set the feed at any time (linear, exponential, pulse-wise), or add nutrients when specific conditions are met, such as when a certain biomass concentration is reached or when a nutrient is depleted. The fed-batch process offers a wide range of control strategies and is also suitable for highly specialized applications. However, it may increase the processing time and potentially leads to inhibition through the accumulation of toxic by-products. At high cell density, limitation through limited oxygen transfer from the gas phase may also occur.

Preferably, in the method of the present invention the submerged fermentation is operated as a continuous process. After a batch growth phase, an equilibrium is established with respect to a particular component (also called steady state). Under these conditions, as much fresh culture medium is added, as it is removed (chemostat). These bioprocesses are referred to as continuous cultures, and are particularly suitable when an excess of nutrients would result in inhibition due to e.g. acid or ethanol build up or excessive heating. Other advantages of this method include reduced product inhibition and an improved space-time yield. When medium is removed, cells are harvested, which is why the inflow and outflow rates must be less than the doubling time of the microorganisms. Alternatively, the cells can be retained in a wide variety of ways (for example, in a spin filter), which is called perfusion. In a continuous process, the space-time yield of the bioreactor can be even further improved compared to that of a fed-batch process. However, the long cultivation period also increases the risk of contamination and long-term changes in the cultures. The three most common types of continuous culture are chemostat (The rate of addition of a single growth-limiting substrate controls cell multiplication), turbidostat (an indirect measurement of cell numbers-turbidity or optical density-which needs an additional sensor but is driven by real-time feedback, controls addition and removal of liquid), and perfusion (this type of continuous bioprocessing mode is based on either retaining the cells in the bioreactor or recycling the cells back to the bioreactor; fresh medium is provided and cell-free supernatant gets removed at the same rate).

Thus preferably, step (a) is performed as a continuous process. Preferably, the process is performed with a dilution rate of at least 0.85 $h^{-1}$, preferably of at least 1.1 $h^{-1}$, more preferably at least 1.2 $h^{-1}$, even more preferably at least 1.4 $h^{-1}$, wherein the growth rate in process of each of the at least one microorganism strain(s) of step (a) is limited by the dilution rate. With high dilution rate, exceeding the growth rate of most of potential contaminants. Because the dilution rate is higher than the growth rate of most of the microorganisms that could be potential contaminants, they will be automatically washed out the fermenter before they can propagate in the fermenter. As a consequence, the cultivation may be performed under non-sterile conditions. Therefore, in certain embodiments of the present invention, step (a) is performed as a continuous. Preferably, the process is performed with a dilution rate of at least 0.85 $h^{-1}$, preferably of at least 1.1 $h^{-1}$, more preferably at least 1.2 $h^{-1}$, even more preferably at least 1.4 $h^{-1}$, wherein the growth rate in process of each of the at least one microorganism strain(s) of step (a) is limited by the dilution rate and optionally wherein the at least one microorganism strain(s) is cultivated under non-sterile conditions. Non-sterile conditions are understood herein as the conditions wherein the fermenter has not been sterilized, e.g. by autoclavation, and/or the medium has not been sterilized e.g. by autoclavation, by filtration or by any other method known to the skilled person. In certain embodiments, as understood herein, the medium may be sterilized or pasteurized, however the fermenter may be used not sterilized. It is further noted that while under these conditions other microorganisms—beyond the at least one microorganism strain of the present invention—could grow, they are out-competed (or out-grown) by the at least one microorganism strain of the present invention.

In one embodiment, step (a) is performed as a continuous fermentation of at least one microorganism strain(s), performed with a dilution rate of at least 0.85 $h^{-1}$, preferably of at least 1.1 $h^{-1}$, more preferably at least 1.2 $h^{-1}$, even more preferably at least 1.4 $h^{-1}$, wherein the at least one microorganism strain(s) comprises *Vibrio natriegens* or *Geobacillus* strain. In one embodiment, step (a) is performed as a continuous fermentation of at least one microorganism strain(s), performed with a dilution rate of at least 0.85 $h^{-1}$, preferably of at least 1.1 $h^{-1}$, more preferably at least 1.2 $h^{-1}$, even more preferably at least 1.4 $h^{-1}$, wherein the at least one microorganism strain(s) comprises a vitamin B12 autotroph, preferably *Bacillus megaterium.*

In one embodiment, step (a) involves recycling of the cells of at least one microorganism strain.

In certain embodiments, step (a) of the present invention may involve co-cultivation of more than one microorganism strain(s), wherein at least one strain does not show the growth rate in the process of at least 0.85 $h^{-1}$. Such an embodiment is encompassed within the scope of the present invention only when at least one microbial strain has a growth rate in the process of at least 0.85 $h^{-1}$, preferably of at least 1.1 $h^{-1}$, more preferably at least 1.2 $h^{-1}$, even more preferably at least 1.4 $h^{-1}$, In the case of co-cultivation of more than one microorganism, the growth rate may refer to a combined growth rate of all the microorganism in the culture, and describe the increase in combined biomass over time.

Once cultivating is complete, the biomass is harvested according to the methods known to the skilled person. Harvesting the biomass may include separation and/or washing. The state-of-the art separation techniques employ tangential flow filtration or industrial (nozzle or centrifugal) separators. The biomass obtainable as described herein has a dry mass between 10 and 25% (as defined in weight to weight ratio expressed as percentage, % w/w).

The biomass as obtainable herein is used in the step (b) of the method of the present invention for the production of a composition comprising at least 15% nucleotides, preferably at least 18% nucleotides, more preferably at least 22% nucleotides and at least 40% amino acids and peptides. However, the said biomass is also usable in other processes and applications, as conceivable to the skilled person. Thus, it is noted that in another aspect the present invention relates to a biomass, as obtainable herein.

Step (b) of the method of the present invention for the production of a composition comprising at least 15% nucleotides, preferably at least 18% nucleotides, more preferably at least 22% nucleotides and at least 40% amino acids and peptides comprises lysing the cells present in the biomass of step (a). Any method known to the skilled person that is industrially applicable can be used herein. The productions of extracts encompassed within the scope of the present invention can be done for example by a mechanical or chemical disruption followed by diverse enzymatic treatments and an inactivation of the biomass prior to enzymatic treatment with diverse enzymes.

In certain embodiments, mechanical disruption methods like bead mill or PEF are used, particularly if the at least one microorganism strain(s) is a gram-negative bacteria. Chemical methods for breaking down the cells can also be used within the scope of the present invention. It is noted that the method of lysing the cells as discussed herein may be adapted based on the microorganism. For example, when gram-negative bacterium/bacteria are used, they are easier to lyse than gram-positive bacteria, e.g. *Geobacillus* strains or *Bacillus megaterium*. Further compared to yeast extracts or plant cells, bacteria have a thinner cell wall that is easier to break during the lysis process (it is particularly true for. gram-negative bacteria, like *Vibrio natriegens*). It is noted that lysis of such cells is more efficient than that of yeast or plant cells.

Chemical method for breaking down the cells include, but are not limited to, treatment with salt(s), basic reagent(s) detergent(s) and/or surfactant(s). It is noted that chemical methods, in particular those involving basic reagent(s), also referred to as alkali reagent(s), may lead to partial degradation of nucleic acid, for example to degradation of RNA and formation of 2'-ribonucleotides and 3'-ribonucleotides.

Optionally, heat pre-treatment of the biomass can be performed before the lysis or homogenization. Heat pre-treatment is typically performed at a temperature of between 70° C. and 180° C. and/or for a time of between 10 minutes and 360 minutes. Skilled person will be able to adjust the conditions of the heat pre-treatment to the biomass at issue and experimental setup. Whether or not heat pre-treatment is required depends on the planned further processing. If the biomass is to be lysed by mechanical homogenization, as described herein, the thermal pre-treatment is preferably performed. Without wishing to be bound by the theory, it is noted that the purpose of thermal pre-treatment is deactivation of the enzymes of the at least one microorganism strain(s). Preferably, if the biomass is to be lysed by mechanical homogenization, the thermal pre-treatment step is to be kept short, preferably less than 30 minutes, more preferably less than 15 minutes. As understood herein, longer time of the thermal pre-treatment.

Thus, in a particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (b) is performed by mechanical homogenization, and optionally involves heat pre-treatment performed at a temperature of between 70° C. and 180° C. and/or for a time of between 10 minutes and 360 minutes.

Alternatively, the cell lysis can be performed by autolysis. Autolysis is the process of letting the microorganisms destruct themselves as the temperature gets higher than their optimum temperature. The process involves the production by the microorganisms of specific enzymes that will destroy protein or other components that are denatured at higher temperature for instance.

For path involving autolysis, the biomass undergoes a process of self-degradation induced by a thermal treatment for 0.1 to 48 hours at temperatures between 45° C. and 200° C. It will be obvious to people acquainted with the art of autolysing microorganisms that the temperature and incubation has to be chosen according to the nature of the said microorganisms, e.g. thermophile and mesophilic bacteria will have different autolysis temperatures and gram-positive and gram-negative bacteria require different incubation time because of the different structure of their cell walls. Similarly, treating the same biomass for different times or at different temperature will also produce different extract compositions.

Preferably, in the method for the production of a composition comprising at least 15% nucleotides, preferably at least 18% nucleotides, more preferably at least 22% nucleotides and at least 40% amino acids and peptides of the present invention, the cell lysis in step (b) is not performed by autolysis.

In case of path involving a mechanical or chemical disruption followed by diverse enzymatic treatments, the biomass is subjected to mechanical or chemical disruption to break down the cell wall in a first step and the obtained cell components are then treated directly with an enzyme cocktail containing proteolytic enzymes, nuclease, AMP deaminase or a combination thereof.

As understood herein, the composition of the present invention may in certain embodiments comprise the cell wall. However, also encompassed by the present invention are compositions wherein the cell wall was removed from the composition, according to the methods known to the skilled person. Preferably, removal of the cell wall is to take place together or after the step (b) of the method of the present invention.

As known to the skilled person, steps (b) and (c) may involve autolysis of the cells of the at least one microbial strain(s) contained in the biomass of step (a), wherein the autolysis is preferably performed at a temperature of between 40° C. and 200° C. and/or at a pH of between 3.0 and 9.0, and/or for a time of between 10 minutes to 72 hours. In certain embodiments, the method for production of a composition of the present invention, wherein steps (b) and (c) involve autolysis of the cells of the at least one microbial strain(s) contained in the biomass of step (a), may result in a composition comprising a least 1.5% nucleotides, preferably at least 2.5% nucleotides, more preferably at least 3.5% nucleotides, even more preferably at least 5% nucleotides. The final nucleotide content will depend, among others, on the nucleotide content of the biomass of step (a). It is to be understood that if the steps (b) and (c) involve autolysis of the cells of the at least one microbial strain(s) contained in the biomass of step (a), no heat pretreatment step is required. Thus, in these embodiments, preferably no heat pretreatment step, as disclosed herein, is to be performed.

In certain embodiments of the present invention, the method for the production of a composition comprising at least 15% nucleotides, preferably at least 18% nucleotides, more preferably at least 22% nucleotides and at least 40% amino acids and peptides of the present invention, step (b) involves heat pre-treatment followed by enzymatic treatment with protease(s). As understood herein, the heat pretreatment step is preferably performed at a temperature of between 70° C. and 180° C. and/or for a time of between 10 minutes and 360 minutes. The enzymatic treatment with protease(s) is preferably performed at a temperature of between 40° C. and 100° C., more preferably between 45° C. and 70° C. The enzymatic treatment with protease(s) is further preferably performed at a pH of between 3.0 and 9.0, more preferably between 5.0 and 7.0. The enzymatic treatment with protease(s) is preferably performed at a time of between 0.5 and 72 hours, more preferably between 0.5 and 10 hours. It is noted that preferably enzymatic treatment occurs after heat pre-treatment, as described herein. Any protease enzyme as known to the skilled person can be used in the enzymatic treatment with protease(s) as described herein. The skilled person will be able to select appropriate protease or protease cocktail, also referred to as proteases, and also to determine the optimal loading of the protease(s). Preferably, proteases are used at 0.01 to 5% (w/w) with respect to the total weight of the biomass.

It is known by the skilled person that RNA in the cell is in part complexed with proteins (among others, RNA polymerase and sigma factor). It is therefore possible that not all RNA is readily available to the nucleases, hampering a full conversion from RNA into nucleotides and nucleosides. Adequate treatment with a protease prior to nuclease enzymatic treatment may degrade the RNA-protein complexes and may improve the nucleotide yield.

It is further noted herein that upon heat pre-treatment followed by enzymatic treatment with protease(s) the cell wall remains in the reaction mixture, and preferably needs to be separated. The separation can be performed by the means of mechanical and/or physical separation. Without wishing to be bound by the theory, it is understood herein that heat pre-treatment followed by enzymatic treatment with protease(s) leads to cell lysis.

The present inventors have surprisingly found that the nucleic acid content in the microbial strain(s) as used in the present invention, in particular in bacteria, is so high that separation of the nucleic acid from other cell components to produce extracts rich in nucleotides can be dispensed with. In other words, the present inventors have demonstrated, that by using the microbial strain(s) with high nucleic acid content the extracts with nucleotide content can be obtained, that otherwise would only be obtainable in the process comprising the step(s) of separation and/or concentration of nucleic acid.

In certain embodiments of the present invention separation of the nucleic acids and optionally of the protein from other components of obtained extracts/lysates can be performed as an optional step of the method of the present invention. Preferably, said separation can be performed by using state-of-the-art ultrafiltration method with a cutoff between 10 to 50 kD. Alternatively, magnetic beads can be employed to produce extracts with even higher nucleotide concentration or pure nucleotides of interest.

In both embodiments, the nucleic acid is recovered in the retentate but in the latter case, the nucleic acids specifically bind to the beads and are eluted later, thus leading to obtaining a nucleic acid fraction of high purity. In the case of ultrafiltration, as known to the skilled person an additional purification step can be foreseen to increase purity of recovered nucleic acids. In certain alternative embodiments, the extracts with even higher nucleotide concentration or substantially pure nucleotides of interest can be obtained by the means of chromatography, in particular ion exchange chromatography. In certain embodiments, the extracts with even higher nucleotide concentration can be obtained through removal of impurities upon active carbon treatment. In certain alternative embodiments, the extracts with even higher nucleotide concentration or substantially pure nucleotides of interest can be obtained by the means of crystallization. In certain embodiments, the extracts with even higher nucleotide concentration or substantially pure nucleotides of interest can be obtained by the means involving a combination of the means as disclosed hereinabove.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (c) involves enzymatic treatment with nuclease(s). Preferably the said enzymatic treatment with nuclease is performed at a temperature of between 40° C. and 100° C., more preferably between 45° C. and 70° C. Preferably the said enzymatic treatment with nuclease is performed at a pH of between 3.0 and 9.0, more preferably between 5.0 and 7.0. Preferably the said enzymatic treatment with nuclease is performed at a time of between 0.5 and 72 hours, more preferably between 0.5 and 10 hours. Any nuclease enzyme as known to the skilled person can be used in the enzymatic treatment with nuclease(s) as described herein. The skilled person will be able to select appropriate nuclease or nuclease cocktail, also referred to as nucleases, and also determine the optimal loading of the nuclease(s). Preferably, nucleases are used at the loading of 0.01 to 5% (w/w) with respect to the total weight of the lysate.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (c) further comprises enzymatic treatment with deaminase(s). Preferably enzymatic treatment with deaminase(s) is performed at a temperature of between 40° C. and 100° C., more preferably between 45° C. and 70° C. Preferably, enzymatic treatment with deaminase(s) is performed at a pH of between 3.0 and 9.0, more preferably between 5.0 and 7.0. Preferably, enzymatic treatment with deaminase(s) is performed for a time of between 0.5 and 72 hours, more preferably between 0.5 and 10 hours. Any deaminase enzyme as known to the skilled person can be used in the enzymatic treatment with deaminase(s) as described herein. The skilled person will be able to select appropriate deaminase or deaminase cocktail, also referred to as deaminases. Preferably, deaminases are used at the loading of 0.01 to 5% (w/w) with respect to the total weight of the lysate.

According to the present invention, the steps of the enzymatic treatment with nuclease(s) and of the enzymatic treatment with deaminase(s) can be performed separately, sequentially or together. In case of sequential application, an additional step of thermal deactivation of the enzyme used first, before the addition of the second enzyme, as known to the skilled person, can be optionally included. Preferably, the steps of the enzymatic treatment with nuclease(s) and of the enzymatic treatment with deaminase(s) are performed together. Such treatment can also be referred to as treatment with nuclease(s) and deaminase(s). The selection of particular nuclease(s) and deaminase(s) is to be executed by the skilled person so that the enzymes can show specific activity and preferably no non-specific activity under conditions of the treatment. As discussed herein, preferably treatment with nuclease(s) and deaminase(s) is performed at a temperature of between 40° C. and 100° C., more preferably between 45° C. and 70° C. Preferably, treatment with nuclease(s) and deaminase(s) is performed at a pH of between 3.0 and 9.0, more preferably between 5.0 and 7.0. Further preferably treatment with nuclease(s) and deaminase(s), enzymatic treatment with deaminase(s) is performed for a time of between 0.5 and 72 hours, more preferably between 0.5 and 10 hours. Particularly preferred are enzymes that tolerate high salt (e.g. NaCl) concentrations, e.g., over 3% w/w, 5% w/w, over 7% w/w, or over 9% w/w.

While plant-based proteins from various sources like pea, soy or wheat have been introduced as a replacement to animal-based proteins both for human consumption and animal feed, they have several disadvantages. Firstly, most plant materials do not provide complete protein (as understood according to FAO definition—fao.org, as well as definition of complete protein on en.wikipedia.org/wiki/Complete_protein, as accessed on Mar. 11, 2021) and often contain antinutritive compounds (e.g. saponins). Incomplete protein and antinutrients are reducing feed effectiveness or triggering the need for supplementing animal-based proteins like fish or whey in animal feed. In human food, it can induce amino acid deficiencies in vegan-based diets. Secondly, the protein concentration in plants is relatively low (5-30%) and proteins are contained in a rigid plant cell structure. Therefore, equipment with high energy needs like jet or air classifying mills is required to separate protein fractions and concentrate them to a viable content of 80% protein. The present invention is overcoming these challenges by cultivating fast-growing microbes, in particular bacteria, that contains high concentrations of complete proteins (over 40%) and has a thinner cell wall.

In again a further particular aspect, the method for the production of a composition comprising at least 15% nucleotides, preferably at least 18% nucleotides, more preferably at least 22% nucleotides and at least 40% amino acids and peptides of the present invention relates to an embodiment, wherein step (c) further comprises enzymatic treatment with protease(s). Preferably, enzymatic treatment with protease(s) is performed at a temperature of between 40° C. and 100° C., more preferably between 45° C. and 70° C. Preferably, enzymatic treatment with protease(s) is performed at a pH of between 3.0 and 9.0, more preferably between 5.0 and 7.0. Further preferably, enzymatic treatment with protease(s) is performed for a time of between 0.5 and 72 hours, more preferably between 0.5 and 10 hours. Any protease enzyme as known to the skilled person can be used in the enzymatic treatment with protease(s) as described herein. The skilled person will be able to select appropriate protease or protease cocktail, also referred to as proteases. Preferably, the protease(s) as defined herein comprise alcalase and/or papain. Furthermore, the skilled person will also be able to determine the optimal loading of the protease(s). Preferably, proteases are used at 0.01 to 5% (w/w) with respect to the total weight of the lysate.

As known to the skilled person, the product of the step (c) may further undergo additional processes. The composition may be further blended with other compositions and/or supplements, proteins, nucleic acids, vitamins. It may be necessary to perform, according to the methods known to the skilled person, odour neutralization. A suitable technique therefor would be filtration of the composition or the solution of the composition through active carbon filter. The composition may be further sterilized, for example by application of the pulsed electric field, as known to the skilled person. In one embodiment, the composition may be further pasteurized, for example it may undergo high pressure pasteurization. The composition of the present invention may further undergo drying and removal of water, for example by spray drying, band drying, or drum drying.

The present invention in further aspects also refers to a composition comprising at least 15% nucleotides, preferably at least 18% nucleotides, more preferably at least 22% nucleotides and at least 40% protein and/or amino acids and peptides, obtainable according to the method for the production of a composition comprising at least 15% nucleotides, preferably at least 18% nucleotides, more preferably at least 22% nucleotides and at least 40% amino acids and peptides of the present invention. Preferably, the said composition is characterized in IMP/GMP content of at least 11%, preferably at least 13%, even more preferably at least 15%, most preferably at least 17%. IMP and GMP are the major nucleotides contributing to the taste properties, and/or taste enhancement properties of the composition of the present invention.

In certain embodiments, the composition further comprises further compounds that can contribute to taste properties and/or to taste enhancement properties of the composition of the present invention. One such compounds known to the skilled person is glutamate. Glutamate is herein understood as any form of glutamic acid or its salts, as encompassed by this definition. Glutamine is also herein understood to be encompassed by the term "glutamate". Therefore, as understood herein, the term glutamate refers to glutamic acid or its salts or to glutamine or its salts. Thus, in certain embodiments the composition further comprises glutamate content of at least 6% w/w, preferably of at least 8% w/w, more preferably of at least 10% w/w, even more preferably of at least 12% w/w, even more preferably of at least 14% w/w, most preferably of at least 16% w/w. Without wishing to be bound by the theory, it is noted that the main source of glutamate is amino acids and peptides present in the composition of the present invention.

The composition of the present invention comprising at least 15% nucleotides, preferably at least 18% nucleotides, more preferably at least 22% nucleotides and at least 40% protein and/or amino acids and peptides is useful in production of further products, including food products. The food or feed product is defined herein as any product suitable for oral consumption, preferably food, feed, drink or a supplement for food or feed. Thus, the food or feed product should preferably have a taste acceptable to the animal species for which it is intended. Thus, the composition of the present invention is useful in the production of animal feed, pet food, fermentation medium or supplement, food products, nutraceuticals, pharmaceuticals, diagnostic agents, DNA or RNA, or flavour enhancers.

The composition of the present invention comprising at least 15% nucleotides, preferably at least 18% nucleotides, more preferably at least 22% nucleotides and at least 40% protein and/or amino acids and peptides is useful in production of animal feed or pet food. Animal feed is herein defined as food product intended for nutrition of preferably domestic animals, especially of livestock. It can for example be manufactured in the solid form, e.g. in the form of pellets, or in any other suitable form for feeding animals. Pet food as defined herein is intended for small domestic animals, including dogs, cats, mice, guinea pigs, domestic birds, aquarium fish. However, this list is not meant to be in any way limiting.

The composition of the present invention comprising at least 15% nucleotides, preferably at least 18% nucleotides, more preferably at least 22% nucleotides and at least 40% protein and/or amino acids and peptides is useful in production of fermentation medium or supplement. Fermentation medium is understood herein as a substrate or a source of nutrients on which the microbial strain(s) can grow, in particular be cultivated in a controlled way for, for example, laboratory or biotechnological purposes. Fermentation supplement is herein understood as a product that is added to the fermentation medium, but is not required to be able to support the growth of the microbial strain on its own.

The composition of the present invention comprising at least 15% nucleotides, preferably at least 18% nucleotides, more preferably at least 22% nucleotides and at least 40% protein and/or amino acids and peptides is useful in production of a nutraceutical. Nutraceutical, which also may be referred to as functional food as understood herein is defined as any food that goes beyond simple nutrition and has at least one specific targeted action to improve the health and/or well-being of the host and/or prevent pathological states in the host.

In again a further aspect, the present invention relates to animal feed, pet food, food product, fermentation medium or supplement, nutraceutical or flavour enhancer comprising the composition comprising at least 15% nucleotides, preferably at least 18% nucleotides, more preferably at least 22% nucleotides and at least 40% protein and/or amino acids and peptides of the present invention. In other words, the present invention relates to animal feed, pet food, food product, fermentation medium or supplement, nutraceutical or flavour enhancer produced using the composition comprising at least 15% nucleotides, preferably at least 18% nucleotides, more preferably at least 22% nucleotides and at least 40% protein and/or amino acids and peptides of the present invention.

In a further aspect, the present invention relates to use of the composition comprising at least 15% nucleotides, preferably at least 18% nucleotides, more preferably at least 22% nucleotides and at least 40% protein and/or amino acids and peptides of the present invention as a monosodium glutamate replacement or as/in an antibiotic replacement.

In a further aspect, the present invention relates to use of the composition comprising at least 15% nucleotides, preferably at least 18% nucleotides, more preferably at least 22% nucleotides and at least 40% protein and/or amino acids and peptides of the present invention for the production of pharmaceuticals, diagnostic agents, DNA or RNA.

In again a further aspect, the present invention also relates to a biomass obtainable in step (a) of the method according for the production of a composition comprising at least 15% nucleotides, preferably at least 18% nucleotides, more preferably at least 22% nucleotides and at least 40% amino acids and peptides of the present invention. The biomass of the present invention, as understood herein, is obtainable by cultivating at least one microorganism strain(s) characterized by a growth rate in the process of at least 0.85 $h^{-1}$. Preferably, the at least one microorganism strain(s) of step (a) is/are characterized by a growth rate in process of at least 1.1 $h^{-1}$, preferably at least 1.2 $h^{-1}$, more preferably at least 1.4 $h^{-1}$. The growth rate as understood herein, unless stated otherwise, is the growth rate in the process, as defined herein. As understood herein, in certain embodiments cultivation is performed as a process. Preferably, the process is performed with a dilution rate of at least 0.85 $h^{-1}$, preferably of at least 1.1 $h^{-1}$, more preferably at least 1.2 $h^{-1}$, even more preferably at least 1.4 $h^{-1}$, wherein the growth rate in process of each of the at least one microorganism strain(s) is limited by the dilution rate. Suitable microorganism strain(s) include, but are not limited to *Vibrio natriegens, Geobacillus* and *Bacillus* strains. Thus, the biomass of the present invention preferably comprises a microorganism strain selected from *Vibrio natriegens, Geobacillus* and *Bacillus* strains. In further preferred embodiments, the glutamate content is at least 5% w/w, preferably at least 6% w/w, more preferably at least 7% w/w, even more preferably at least 8% w/w, even more preferably at least 9% w/w, even more preferably at least 10% w/w, most preferably at least 12% w/w.

In a further aspect, the present invention relates to a single cell protein comprising the biomass of the present invention. The biomass is as defined herein and above. The single cell protein, as understood herein, refers to edible microorganisms, preferably single cell microorganisms. The single cell protein of the present invention is useful in the production of animal feed, pet food or food products, preferably animal feed. The single cell protein as defined herein can further undergo heat treatment, as described herein. It is noted that, without wishing to be bound by the theory, the thermal pre-treatment enables reduction of nucleic acid content to a level acceptable for production of food products or for consumption as food. In certain embodiment, the heat treatment may also be understood as inducing autolysis in the cells forming the single cell protein, as described herein.

In again a further aspect, the present invention relates to a cell lysate obtainable in step (b) of the method for the production of a composition comprising at least 15% nucleotides, preferably at least 18% nucleotides, more preferably at least 22% nucleotides and at least 40% amino acids and peptides of the present invention.

In certain embodiments, the present invention relates to a cell lysate, obtainable in the method as described herein, wherein the steps (b) and (c) involve autolysis of the cells of the at least one microbial strain(s) contained in the biomass of step (a).

In again a further aspect, the present invention relates to a composition comprising nucleotides obtainable by separation, preferably by ultrafiltration, of the cell lysate of the present invention. Preferably, the composition comprising nucleotides comprises at least 22% nucleotides, preferably at least 25% nucleotides, more preferably at least 30% nucleotides. Preferably, the composition comprising nucleotides as defined herein is characterized in IMP/GMP content of at least 11%, preferably at least 13%, even more preferably at least 15%, most preferably at least 17%.

In again a further aspect, the present invention relates to a composition comprising amino acids and peptides obtainable by separation, preferably by ultrafiltration or by using magnetic beads, more preferably by ultrafiltration, of the cell lysate of the present invention. In certain aspects, the separation step, as understood herein, may be understood as concentration step.

In again a further aspect, the present invention relates to use of the composition comprising nucleotides obtainable in a process comprising the step of separation, preferably by ultrafiltration, of the cell lysate of the present invention or the composition comprising amino acids and peptides obtainable in a process comprising the step of separation, preferably by ultrafiltration, of the cell lysate of the present invention in the production of animal feed, pet food, food products, fermentation medium or supplement, nutraceuticals, pharmaceuticals, diagnostic agents, DNA or RNA, or flavour enhancers. As understood herein, the step of separation relates to separation of nucleic acid and proteins, respectively, contained in the lysate, the product of step (b) of the method of the present invention, which is typically followed by (c) converting the nucleic acid present in the lysate of step (b) to nucleotides and optionally converting protein present in the lysate of (b) to amino acids and peptides. The separation step, as understood herein, may also be understood as concentration step. Preferably, the composition comprising nucleotides as defined herein is characterized in IMP/GMP content of at least 11%, preferably at least 13%, even more preferably at least 15%, most preferably at least 17%. IMP and GMP are the major nucleotides contributing to the taste properties, and/or taste enhancement properties of the composition of the present invention. It is further noted that in certain embodiments, the composition comprising nucleotides as described herein, and the composition comprising amino acids and peptides, as described herein, may be used together in the production of animal feed, pet food, food products, fermentation medium or supplement, nutraceuticals, pharmaceuticals, diagnostic agents, DNA or RNA, or flavour enhancers.

In again a further aspect, the present invention relates to animal feed, pet food, food product, fermentation medium or supplement, nutraceutical or flavour enhancer comprising the composition comprising nucleotides obtainable in a process comprising the step of separation, preferably by ultrafiltration or by using magnetic beads, more preferably by ultrafiltration, of the cell lysate of the present invention or the composition comprising amino acids and peptides obtainable in a process comprising the step of separation, preferably by ultrafiltration or by using magnetic beads, more preferably by ultrafiltration, of the cell lysate of the present invention. The process comprising the step of separation is as described hereinabove. As understood herein, the step of separation relates to separation of nucleic acid and proteins, respectively, contained in the lysate, the product of step (b) of the method of the present invention, which is typically followed by (c) converting the nucleic acid present in the lysate of step (b) to nucleotides and optionally converting protein present in the lysate of (b) to amino acids and peptides.

Further aspects and/or embodiments of the invention are disclosed in the following numbered items.

1. A method for the production of a composition comprising at least 22% nucleotides and at least 40% amino acids and peptides, the method comprising the steps of:
   (a) providing biomass by cultivating at least one microorganism strain(s) characterized by a growth rate in the process of at least 0.85 $h^{-1}$,
   (b) lysing the cells present in the biomass of step (a), and
   (c) converting the nucleic acid present in the lysate of step (b) to nucleotides and optionally converting protein present in the lysate of (b) to amino acids and peptides, wherein % are understood as w/w % of dry mass excluding NaCl.
2. The method according to item 1, wherein the at least one microorganism strain(s) of step (a) is/are characterized by a growth rate in process of at least 1.1 $h^{-1}$, preferably at least 1.2 $h^{-1}$, more preferably at least 1.4 $h^{-1}$.
3. The method according to item 1 or 2, wherein the at least one microorganism strain(s) of step (a) is/are characterized by a nucleic acid content of at least 22%, preferably of at least 25%, even more preferably at least 28%.
4. The method according to any one of items 1 to 3, wherein the at least one microorganism strain(s) of step (a) comprises a bacterial strain, preferably a halophile or a thermophile, preferably wherein a bacterial strain is characterized by a genomic G/C content of at least 40%, more preferably of at least 45%, even more preferably of at least 50%, most preferably of at least 55%.

5. The method according to any one of items 1 to 4, wherein the at least one microorganism strain(s) of step (a) comprises a microorganism that is a vitamin B12 autotroph.
6. The method according to any one of items 1 to 5, wherein step (a) is performed as a continuous process with a dilution rate of at least 0.85 $h^{-1}$, preferably of at least 1.1 $h^{-1}$, more preferably at least 1.2 $h^{-1}$, even more preferably at least 1.4 $h^{-1}$, wherein the growth rate in process of each of the at least one microorganism strain(s) of step (a) is limited by the dilution rate, and optionally wherein the at least one microorganism strain(s) is cultivated under non-sterile conditions.
7. The method according to anyone of items 1 to 6, wherein the at least one microorganism strain(s) of step (a) are two microorganism strains, preferably two bacterial strains, further preferably wherein at least one bacterial strain is a vitamin B12 autotroph.
8. The method according to any one of items 1 to 7, wherein the at least one microorganism strain(s) comprises a microorganism strain selected from *Vibrio* spp, in particular *Vibrio natriegens, Geobacillus* spp, in particular *Geobacillus* LC300, and *Bacillus* spp, in particular *Bacillus megaterium.*
9. The method according to any one of items 1 to 8, wherein the at least one microorganism strain(s) comprises a microorganism able to synthesize omega-3 fatty acids.
10. The method according to any one of items 1 to 9, wherein the at least one microorganism strain(s) comprises a genetically modified microorganism.
11. The method according to any one of items 1 to 10, wherein step (b) involves heat pre-treatment performed at a temperature of between 70° C. and 180° C. and/or for a time of between 10 minutes and 360 minutes, followed by enzymatic treatment with protease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.
12. The method according to any one of items 1 to 10, wherein step (b) is performed by mechanical homogenization, and optionally involves heat pre-treatment performed at a temperature of between 70° C. and 180° C. and/or for a time of between 10 minutes and 360 minutes.
13. The method according to any one of items 1 to 12, wherein step (c) involves enzymatic treatment with nuclease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.
14. The method according to any one of items 1 to 13, wherein step (c) further comprises enzymatic treatment with deaminase(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.
15. The method according to any one of items 1 to 14, wherein step (c) further comprises enzymatic treatment with protease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.
16. A composition comprising at least 22% nucleotides and at least 40% protein and/or amino acids and peptides, obtainable according to the method of any one of items 1 to 15.
17. The composition of item 16, characterized in IMP/GMP content of at least 11%, preferably at least 13%, even more preferably at least 15%, most preferably at least 17%.
18. The composition of item 16 or 17, further comprising glutamate content of at least 6% w/w, preferably of at least 8% w/w, more preferably of at least 12% w/w, even more preferably of at least 14% w/w, most preferably of at least 16% w/w.
19. Use of the composition of any one of items 16 to 18 in the production of animal feed, pet food, fermentation medium or supplement, food products, nutraceuticals, pharmaceuticals, diagnostics agents, DNA or RNA, or flavour enhancers.
20. Animal feed, pet food, food product, fermentation medium or supplement, nutraceutical, pharmaceuticals, diagnostics agent, DNA or RNA, or flavour enhancer comprising the composition of any one of items 16 to 18.
21. Use of the composition of any one of items 16 to 18 as a monosodium glutamate replacement or as/in an antibiotic replacement.
22. A biomass obtainable in step (a) of the method according to any one of items 1 to 15.
23. The biomass of item 22, wherein the glutamate content is at least 5%, preferably at least 6% w/w, more preferably at least 7% w/w, even more preferably at least 8% w/w, even more preferably at least 9% w/w, even more preferably at least 10% w/w, most preferably at least 12% w/w.
24. A single cell protein comprising the biomass of item 22 or 23.
25. The single cell protein of item 24, that has further undergone heat treatment.
26. Use of single cell protein of item 24 or 25 in the production of animal feed, pet food or food products, preferably animal feed.
27. A cell lysate obtainable in step (b) of the method according to any one of items 1 to 15.
28. A composition comprising nucleotides obtainable by separation, preferably by ultrafiltration, of the cell lysate of item 27.
29. A composition comprising amino acids and peptides obtainable by separation, preferably by ultrafiltration, of the cell lysate of item 27.
30. Use of the composition of item 28 or of the composition of item 29 in the production of animal feed, pet food, food products, fermentation medium or supplement, nutraceuticals, pharmaceuticals, diagnostics agents, DNA or RNA, or flavour enhancers.
31. Animal feed, pet food, food product, fermentation medium or supplement, nutraceutical, pharmaceuticals, diagnostics agents, DNA or RNA, or flavour enhancer comprising the composition of item 28 or the composition of item 29.

Further examples and embodiments of the invention are disclosed in the following numbered paragraphs.

1. A method for the production of a composition comprising at least 22% nucleotides and at least 40% amino acids and peptides, the method comprising the steps of:
   (a) providing biomass by cultivating at least one microorganism strain(s) characterized by a growth rate in the process of at least 0.85 $h^{-1}$,
   (b) lysing the cells present in the biomass of step (a), and
   (c) converting the nucleic acid present in the lysate of step (b) to nucleotides and optionally converting protein present in the lysate of (b) to amino acids and peptides, wherein % are understood as w/w % of dry mass excluding NaCl.
2. The method according to paragraph 1, wherein the at least one microorganism strain(s) of step (a) is/are characterized by a growth rate in process of at least 1.1 $h^{-1}$, preferably at least 1.2 $h^{-1}$, more preferably at least 1.4 $h^{-1}$,
   and/or
   wherein the at least one microorganism strain(s) of step (a) is/are characterized by a nucleic acid content of at least 22%, preferably of at least 25%, even more preferably at least 28%,
   and/or
   wherein the at least one microorganism strain(s) of step (a) comprises a bacterial strain, preferably a halophile or a thermophile, preferably wherein a bacterial strain is characterized by a genomic G/C content of at least 40%, more preferably of at least 45%, even more preferably of at least 50%, most preferably of at least 55%.
3. The method according to any one of paragraphs 1 or 2, wherein the at least one microorganism strain(s) of step (a) comprises a microorganism that is a vitamin B12 autotroph,
   or
   wherein the at least one microorganism strain(s) of step (a) are two microorganism strains, preferably two bacterial strains, further preferably wherein at least one bacterial strain is a vitamin B12 autotroph.
4. The method according to any one of paragraphs 1 to 3, wherein step (a) is performed as a continuous process with a dilution rate of at least 0.85 $h^{-1}$, preferably of at least 1.1 $h^{-1}$, more preferably at least 1.2 $h^{-1}$, even more preferably at least 1.4 $h^{-1}$, wherein the growth rate in process of each of the at least one microorganism strain(s) of step (a) is limited by the dilution rate, and optionally wherein the at least one microorganism strain(s) is cultivated under non-sterile conditions.
5. The method according to any one of paragraphs 1 to 4, wherein the at least one microorganism strain(s) comprises a microorganism strain selected from *Vibrio* spp, in particular *Vibrio natriegens, Geobacillus* spp, in particular *Geobacillus* LC300, and *Bacillus* spp, in particular *Bacillus megaterium.*
6. The method according to any one of paragraphs 1 to 5, wherein the at least one microorganism strain(s) comprises a microorganism able to synthesize omega-3 fatty acids,
   and/or
   wherein the at least one microorganism strain(s) comprises a genetically modified microorganism.
7. The method according to any one of paragraphs 1 to 6, wherein step (b) involves heat pre-treatment performed at a temperature of between 70° C. and 180° C. and/or for a time of between 10 minutes and 360 minutes, followed by enzymatic treatment with protease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours,
   and/or
   wherein step (b) is performed by mechanical homogenization, and optionally involves heat pre-treatment performed at a temperature of between 70° C. and 180° C. and/or for a time of between 10 minutes and 360 minutes,
   and/or
   wherein step (c) involves enzymatic treatment with nuclease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours,
   preferably wherein step (c) further comprises enzymatic treatment with deaminase(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours,
   preferably wherein step (c) further comprises enzymatic treatment with protease(s), preferably at a temperature of between 40° C. and 100° C., more preferably between 45° C. and 70° C., and/or at a pH of between 3.0 and 9.0, more preferably between 5.0 and 7.0, and/or for a time of between 0.5 and 72 hours, more preferably between 0.5 and 10 hours.
8. A composition comprising at least 22% nucleotides and at least 40% protein and/or amino acids and peptides, obtainable according to the method of any one of paragraphs 1 to 7,
   preferably characterized in IMP/GMP content of at least 11%, preferably at least 13%, even more preferably at least 15%, most preferably at least 17%,
   preferably further comprising glutamate content of at least 6% w/w, preferably of at least 8% w/w, more preferably of at least 12% w/w, even more preferably of at least 14% w/w, most preferably of at least 16% w/w.
9. Use of the composition of paragraph 8 in the production of animal feed, pet food, fermentation medium or supplement, food products, nutraceuticals, pharmaceuticals, diagnostics agents, DNA or RNA, or flavour enhancers.
10. Animal feed, pet food, food product, fermentation medium or supplement, nutraceutical, pharmaceuticals, diagnostics agent, DNA or RNA, or flavour enhancer comprising the composition of paragraph 8.
11. Use of the composition of paragraph 8 as a monosodium glutamate replacement or as/in an antibiotic replacement.
12. A biomass obtainable in step (a) of the method according to any one of paragraphs 1 to 7, preferably wherein the glutamate content is at least 5%, more preferably at least 6% w/w, even more preferably at least 7% w/w, even more preferably at least 8% w/w, even more preferably at least 9% w/w, even more preferably at least 10% w/w, most preferably at least 12% w/w.

13. A single cell protein comprising the biomass of paragraph 12, preferably wherein the biomass has undergone a heat treatment.
14. Use of single cell protein of paragraph 13 in the production of animal feed, pet food or food products, preferably animal feed.
15. A cell lysate obtainable in step (b) of the method according to any one of paragraphs 1 to 7.
16. A composition comprising nucleotides obtainable by separation, preferably by ultrafiltration, of the cell lysate of paragraph 15.
17. A composition comprising amino acids and peptides obtainable by separation, preferably by ultrafiltration, of the cell lysate of paragraph 15.
18. Use of the composition of paragraph 16 or of the composition of paragraph 17 in the production of animal feed, pet food, food products, fermentation medium or supplement, nutraceuticals, pharmaceuticals, diagnostics agents, DNA or RNA, or flavour enhancers.
19. Animal feed, pet food, food product, fermentation medium or supplement, nutraceutical, pharmaceuticals, diagnostics agents, DNA or RNA, or flavour enhancer comprising the composition of paragraph 16 or the composition of paragraph 17.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention is illustrated with the following examples, which however are not meant to be construed as limiting.

EXAMPLES

General Experimental Protocols

I. Fermentation Conditions

To produce the biomass from *V. natriegens* that was used to produce the extracts afterwards, 3×100 mL preculture flasks were prepared with 5 mL of a modified M9 medium derived from Harwood and Cutting (Harwood and Cutting, 1990, Molecular Biological Methods for *Bacillus*. New York, NY: Wiley) and containing 5 g $L^{-1}$ of sugars from beet molasses or glucose, 1 g $L^{-1}$ of $NH_4Cl$, 3 g $L^{-1}$ of $KH_2PO_4$, 0.5 g $L^{-1}$ NaCl, 6.7 g $L^{-1}$ of $Na_2HPO_4$, 1 mg $L^{-1}$ of $MnCl_2 \cdot 4H_2O$, 1.7 mg $L^{-1}$ of $ZnCl_2$, 430 μg $L^{-1}$ of $CuCl_2 \cdot 2H_2O$, 328 μg $L^{-1}$ of $CoCl_2$, 600 μg $L^{-1}$ of $NaMoO_4 \cdot 2H_2O$, 11.1 mg $L^{-1}$ of $CaCl_2$), 30 mg $L^{-1}$ of 3,4-dihydroxybenzoic acid (3,4-DHB), 13.5 mg $L^{-1}$ of $FeCl_3$ and 120 mg $L^{-1}$ of $MgSO_4$. The cultures were incubated at 37° C. and 270 rpm overnight and then collected in a 15 mL falcon tube and centrifuged afterwards (10 min, 4500 rpm, 4° C.). The supernatant was removed, the pellet washed with sterile 0.9% NaCl and the resuspended cell suspension was then used to inoculate a 15 L fermenter with 10 L working volume of the same medium. The fermenter was run at a constant temperature of 37° C. and pH was regulated to 7 during the fermentation course using 25% ammonia. Similarly, the air supply and stirring speed were set 1.5 VVM and 400 rpm at start, respectively, but subsequently increased to keep the dissolved oxygen (DO) at 30% over the whole course of the fermentation. After fermentation, the broth was cooled down directly to 10-15° C. and biomass was separated by centrifugation (4500 rpm, 10 min, 4° C.), washed with 0.9% NaCl and centrifuged again. Biomass was then stored at 4° C. before further processing.

II. Autolysis

For autolysis, the obtained biomass was diluted in water to obtain a suspension with exactly 16% dry mass. Autolysis was then performed by incubating 100 mL of this suspension in a water bath at 49° C. and 150 rpm for 14 hours before the temperature was raised to 56° C. for 6 additional hours. The resulting solution was then centrifuged to remove the cell wall debris and the supernatant-produced extract-transferred to a tube and freeze-dried to get a powder. Composition of the extract was analyzed according to the methods presented herein.

III. Mechanical Lysis Followed by Enzymatic Treatment

Preferably, mechanical lysis followed by enzymatic treatment is to be performed as follows, unless indicated to the contrary. For mechanical lysis, the biomass was resuspended in water to obtain a final dry mass between 9 and 10% that was subsequently homogenized at 1500 bar. During the whole process, the suspension as well as the homogenizer was kept at 4° C. to ensure the stability of nucleic acid. After homogenization, part of the suspension was freeze-dried for analysis of the obtained extract. The other part of the extract was subjected to different enzymatic treatments to convert the protein and nucleic acid from the previous extract into amino acids, peptides, and nucleotides. To do so, 0.4% Nuclease E7 from company Amano enzyme (Japan) were added to the suspension that was subsequently incubated at 65° C. for 16 hours. Subsequently, 0.2% Protease M was added, and the suspension was incubated at 50° C. to convert protein to amino acids.

Alternatively, mechanical lysis followed by enzymatic treatment may also be performed as follows. For mechanical lysis, the biomass was resuspended in water to obtain a final dry mass between 19 and 20% that was subsequently homogenized at 1500 bar. During the whole process, the suspension as well as the homogenizer was kept at 4° C. to ensure the stability of nucleic acid. After homogenization, the cell wall was discarded by centrifugation (4500 rpm. 10 min, 4° C.) and part of the supernatant was freeze-dried for analysis of the obtained extract. The other part of the extract was subjected to different enzymatic treatments to convert the protein and nucleic acid from the previous extract into amino acids, peptides, and nucleotides. To do so, 0.1% (w/w) Deamizyme T, 0.2% Nuclease E7 as well as 0.05% YL-T L from company Amano enzyme (Japan) were added to the suspension that was subsequently incubated at 65° C. for 4 hours. Subsequently, 0.1% Prote AXH was added, and the suspension was incubated at 50° C. to convert protein to amino acids.

Analytical Methods

I. Determination of Protein Content

First, the nitrogen content in the samples was determined using the Kjeldahl method (ASU method L 06.00-7 (2014/08)) and later converted to protein content by multiplying with the factor 6.25, typically applied in the food industry and finally subtracting nucleic acid content as it also contains nitrogen. The total protein content could also be verified with the analysis of the digested amino acid content.

II. Analysis of Amino Acid Content

To the extracts the α-aminobutyrate was added to the final concentration of 200 UM, so that α-aminobutyrate could serve as an internal standard. Amino acid concentrations in the prepared samples were finally measured by fluorescence detection using an Agilent 1200 HPLC system (Agilent technologies, Waldbronn, Germany) equipped with a reverse phase column Gemini 5μ C18 110 A (150×4.6 mm, Phenomenex, Aschaffenburg, Germany) as stationary phase. Separation of the different proteinogenic amino acids relied on a gradual change of the mobile phase composition throughout the measurement, mixing differently eluent A (40 mM NaH2PO4, pH 7.8) and eluent B (45% methanol, 45% acetonitrile, 10% water) according to a well-defined gradient profile. Moreover, column separation was operated at 40° C. with a flow rate of 1 mL $min^{-1}$. In addition, a pre-column (Gemini C18, MAX, RP, 4×3 mm, Phenomenex, Aschaffenburg, Germany) was used to increase column lifetime. Fluorescence detection was achieved through pre-column derivatisation with o-phtalaldehyde (OPA) and 9-fluorenylmethyloxycarbonyl (FMOC) and modification of the excitation and emission wavelength (Table 1).

TABLE 1

Method used for separation and quantification of amino acids - Composition of the mobile phase was varied during measurement to achieved separation by gradient elution. Eluent A: 40 mM $NaH_2PO_4$, pH 7.8; Eluent B: 45% methanol, 45% acetonitrile, 10% water.

| Time [min] | Eluent A [%] | Eluent B [%] | Excitation λ [nm] | Emmision λ [nm] |
|---|---|---|---|---|
| 0 | 100 | 0 | 340 | 450 |
| 40.5 | 59.5 | 40.5 | 340 | 450 |
| 41 | 39 | 61 | 340 | 450 |
| 43 | 39 | 61 | 266 | 305 |
| 57.5 | 0 | 100 | 266 | 305 |
| 59.5 | 0 | 100 | 340 | 450 |
| 60.5 | 25 | 75 | 340 | 450 |
| 61.5 | 50 | 50 | 340 | 450 |
| 62.5 | 75 | 75 | 340 | 450 |
| 63.5 | 100 | 100 | 340 | 450 |
| 65.5 | 100 | 100 | 340 | 450 |

III. Analysis of Ribonucleic Acid (RNA) Content

To determine nucleic acid content, a protocol adapted from Benthin et al. (1991) was used. Shortly, the cells were first washed with 700 mM $HClO_4$ and subsequently digested at 37° C. and 300 min-1 for 80 min with 300 mM KOH. After lysis, the resulting suspensions were cooled and neutralized with 3 M $HClO_4$. The supernatants were then collected by centrifugation (4500 rpm, 4° C., 10 min) and remaining cell debris washed again with 500 mM $HClO_4$ to recover remaining nucleic acids and remove $KClO_4$ precipitate. All supernatants were mixed and the final solutions their nucleic acid content was finally quantified by spectrometric measurement with a NanoDrop 1000™ (Thermo Fisher Scientific, Waltham, MA, USA).

IV. Determination of Deoxyribonucleic Acid (DNA) Content Concentration

To break the cell walls, cell pellets were incubated for 30 min using 560 μL of DNA lysis buffer (s. Table 2) in 2 mL tubes at 30° C. and 350 min-1 and subsequently subjected to a mechanical lysis with glass beads (20% v/v, 0.038-0.045 mm) in a FastPrep-24™ to make sure the cells are completely lysed. The obtained extracts were then centrifuged at 4° C. and 13200 min-1 for 5 min and the supernatant containing cytosolic compounds was collected and treated with 140 μL of a solution containing 60 μg $L^{-1}$ RNase to fully digest the ribonucleic acid in the samples. Subsequently, DNA from the sample was purified using a first separation step with 700 μL Roti-phenol.chloroform-isoamylalcohol followed by a second one with 700 μL chloroform. The supernatant obtained after centrifugation was then supplemented with 65 μL of 3 M sodium acetate (pH 5.5) and ice-cold pure DNA to induce DNA precipitation. After centrifugation the supernatant was discarded and the obtained DNA pellets cleaned with 70% ethanol. Finally, the ethanol was removed by evaporation and the DNA pellet resuspended with 100 μL ultrapure water before its concentration was determined using a Nanodrop 1000™

TABLE 2

Composition of DNA lysis buffer (pH adjusted to 8 with 6M NaOH)

| Component | Concentration [g $L^{-1}$] |
|---|---|
| Sucrose | 3.03 |
| EDTA | 1.31 |
| TRIS | 102.70 |
| Lysozyme | 0.5 $10^{-3}$ |

V. Determination of Nucleotide Concentration

The nucleotide content (preferably herein understood as nucleotide, nucleoside and nucleobase content, more preferably as nucleotide and nucleoside content) in the produced extracts was determined by ion-pair reverse phase high performance liquid chromatography (IPRP-LC) using Agilent 1100 system followed by diode array detection (DAD) at 254 nm. The separation was performed using the Synergy Hydrocolumn as stationary phase and a mobile phase consisting of a mixture of 50 mM phosphate buffer (pH 5.8) and methanol at a flow rate of 0.4 mL/min and a temperature of 20° C. To achieve proper separation of analytes the composition of the mobile phase was varied during the run according to following gradient: 0 to 3 min with 50% methanol; 3 to 12 min with 0-50% methanol and finally 12 to 13.5 min 50% Methanol.

Example 1—Growth of the Biomass of *V. Natriegens*

Biomass of *V. natriegens* was prepared as described herein, by growing it on molasses or on glucose as a carbon source. The growth curves are shown in FIG. 1.

Example 2—Composition of the Biomass of *V. Natriegens*

Using the biomass of Example 1, grown on molasses, total protein content, amino acid profile, as well as DNA and RNA content, were determined by using the methods described above. The results are summarized in Table 3. 90% of all available nucleic acids (RNA and DNA) were RNA.

TABLE 3

Analysis of obtained biomass, including total nitrogen determination according to Kjeldahl method, corresponding Kjeldahl protein calculated based on the nitrogen content, RNA and DNA contents determined as discussed above, and true protein content defined herein as total amount of amino acids measured.

| | |
|---|---|
| N [g/Kg] | 123 |
| Kjeldahl Protein | 77% |
| RNA | 28% |
| DNA | 3% |
| True protein | 59% |

Further information on the composition of the obtained biomass, namely, the amino acid profile, is included in the Table 4.

TABLE 4

Amino acid profile in the biomass of Example 2 (w/w excluding NaCl).

| | |
|---|---|
| Total protein [w/w excluding NaCl] | 59% |
| Asp/Asn | 12% |
| Glu/Gln | 15% |
| Ser | 3% |
| His | 3% |
| Gly | 6% |
| Thr | 5% |
| Arg | 8% |
| Ala | 8% |
| Tyr | 3% |
| Val | 7% |
| Met | 1% |
| Phe | 5% |
| Ile | 7% |
| Leu | 10% |
| Lys | 8% |

Example 3—Composition of Autolysate from *V. Natriegens*

The biomass of Example 1 grown on molasses, was subjected to autolysis, as defined herein. Total protein content, amino acid profile, as well as RNA content, were determined by using the methods described above.

The obtained autolysate contained 2% (w/w) nucleotides, 3% nucleosides and 1% nucleobases. There was also 3% of RNA. This totalled 8% (w/w) of nucleic acids and its derivatives. The total protein content, derived as the sum of all available amino acids, is 54% (w/w). Information on the amino acid profile of the obtained autolysate is included in the Table 5.

TABLE 5

Amino acid profile in the autolysate of Example 3 (w/w excluding NaCl).

| | |
|---|---|
| Total protein [w/w excluding NaCl] | 54% |
| Asp/Asn | 11% |
| Glu/Gln | 16% |
| Ser | 3% |
| His | 2% |
| Gly | 7% |
| Thr | 5% |
| Arg | 7% |
| Ala | 8% |
| Tyr | 2% |
| Val | 7% |
| Met | 1% |
| Phe | 5% |
| Ile | 7% |
| Leu | 9% |
| Lys | 8% |

Example 4—Composition of a Single Cell Protein

The biomass of Example 1 grown on molasses, was subjected to a heat treatment, wherein it was inactivated and further dried. Total protein content, amino acid profile, as well as RNA content, were determined by using the methods described above. The nucleotide content was not determined because no lysis nor enzymatic hydrolysis steps were carried out for production of the single cell protein.

The obtained single cell protein contained 25% RNA (w/w dry weight excluding NaCl). The total protein content, derived as the sum of all available amino acids, is 55% (w/w dry weight excluding NaCl). Information on the amino acid profile of the obtained single cell protein is included in the Table 6. The glutamate content on the single cell protein was 8% (w/w dry weight excluding NaCl).

TABLE 6

Amino acid profile in a single cell protein of Example 4 (w/w excluding NaCl).

| | |
|---|---|
| Total protein [w/w excluding NaCl] | 55% |
| Asp/Asn | 10% |
| Glu/Gln | 15% |
| Ser | 4% |
| His | 2% |
| Gly | 7% |
| Thr | 5% |
| Arg | 6% |
| Ala | 8% |
| Tyr | 3% |
| Val | 7% |
| Met | 2% |
| Phe | 5% |
| Ile | 6% |
| Leu | 8% |
| Lys | 8% |

Example 5—Composition of Lysate after Mechanical Homogenization

The biomass of Example 1 grown on molasses, was subjected to the mechanical homogenization, as defined herein.

The obtained homogenate contained 23% RNA (w/w dry weight excluding NaCl), as determined by using the method described above. The total content of nucleotide, nucleosides and nucleobases in solution was 0.5% (w/w dry weight excluding NaCl).

Example 6—Composition of Enzymatic Extract Produced from Lysate Obtained from Mechanical Homogenization The biomass of Example 1 grown on molasses, was subjected to the mechanical homogenization followed by further enzymatic treatment as defined hereinabove. Total protein content, amino acid profile, as well as RNA content, were determined by using the methods described above.

The enzymatic extract contained 15% (w/w dry weight excluding NaCl) nucleotides, 3% nucleosides and 0.2% nucleobases, totalling 18% (w/w dry weight excluding NaCl) free nucleotides as defined herein. There was still in suspension 6% of RNA, meaning the total of nucleic acids and its derivatives was about 24% (w/w dry weight excluding NaCl).

The total protein content, derived as the sum of all available amino acids, was 53% (w/w). Further information on the amino acid profile of the obtained extract is included in the Table 7. The glutamate content on the enzymatic extract was 7% (w/w dry weight excluding NaCl).

TABLE 7

| Amino acid profile of hydrolysate of Example 6(w/w excluding NaCl). | |
|---|---|
| Total protein [w/w excluding NaCl] | 53% |
| Asp/Asn | 10% |
| Glu/Gln | 14% |
| Ser | 3% |
| His | 2% |
| Gly | 7% |
| Thr | 5% |
| Arg | 6% |
| Ala | 8% |
| Tyr | 2% |
| Val | 7% |
| Met | 2% |
| Phe | 5% |
| Ile | 5% |
| Leu | 8% |
| Lys | 8% |

The invention claimed is:

1. A method for the production of a composition comprising at least 15% nucleotides and at least 40% amino acids and peptides, the method comprising the steps of:

(i) providing biomass by cultivating at least one microorganism strain(s) characterized by a growth rate in the process of at least 0.85 $h^{-1}$, (ii) lysing the cells present in the biomass of step (i), and (iii) converting the nucleic acid present in the lysate of step (ii) to nucleotides and optionally converting protein present in the lysate of (ii) to amino acids and peptides, wherein % are understood as w/w % of dry mass excluding NaCl.

2. The method according to claim 1, wherein (a) the composition comprising at least 15% nucleotides and at least 40% amino acids and peptides is a composition comprising at least 18% nucleotides and at least 40% amino acids and peptides; or (b) the composition comprising at least 15% nucleotides and at least 40% amino acids and peptides is a composition comprising at least 22% nucleotides and at least 40% amino acids and peptides.

3. The method according to claim 1, wherein (a) the at least one microorganism strain(s) of step (i) is/are characterized by a growth rate in process of at least 1.1 $h^{-1}$;

(b) the at least one microorganism strain(s) of step (i) is/are characterized by a nucleic acid content of at least 15%;

(c) the at least one microorganism strain(s) of step (i) comprises a bacterial strain;

(d) the at least one microorganism strain(s) of step (i) comprises a microorganism that is a vitamin B12 autotroph;

(e) step (i) is performed as a continuous process with a dilution rate of at least 0.85 $h^{-1}$, wherein the growth rate in process of each of the at least one microorganism strain(s) of step (i) is limited by the dilution rate, and optionally wherein the at least one microorganism strain(s) is cultivated under non-sterile conditions;

(f) the at least one microorganism strain(s) of step (i) are two microorganism strains;

(g) the at least one microorganism strain(s) comprises a microorganism strain selected from *Vibrio* spp, *Geobacillus* spp, and *Bacillus* spp;

(h) the at least one microorganism strain(s) comprises a microorganism able to synthesize omega-3 fatty acids; and/or (i) the at least one microorganism strain(s) comprises a genetically modified microorganism.

4. The method according to claim 1, wherein (a) step (ii) involves heat pre-treatment performed at a temperature of between 70° C. and 180° C. and/or for a time of between 10 minutes and 360 minutes, followed by enzymatic treatment with protease(s);

(b) step (ii) is performed by mechanical homogenization, and optionally involves heat pre-treatment performed at a temperature of between 70° C. and 180° C. and/or for a time of between 10 minutes and 360 minutes;

(c) step (iii) involves enzymatic treatment with nuclease (s);

(d) step (iii) further comprises enzymatic treatment with deaminase(s); and/or (e) step (iii) further comprises enzymatic treatment with protease(s).

5. A composition comprising at least 15% nucleotides and at least 40% protein and/or amino acids and peptides, obtainable according to the method of claim 1.

6. The composition of claim 5, comprising at least 18% nucleotides or at least 22% nucleotides.

7. The composition of claim 5, (a) characterized in inosine monophosphate (IMP)/guanine monophosphate (GMP) content of at least 11%; and/or (b) further comprising glutamate content of at least 6% w/w.

8. Animal feed, pet food, food product, fermentation medium or supplement, nutraceutical, pharmaceuticals, diagnostics agent, DNA or RNA, or flavour enhancer comprising the composition of claim 5.

9. A monosodium glutamate replacement or an antibiotic replacement, comprising the composition of claim 5.

10. The method according to claim 1, wherein (a) the at least one microorganism strain(s) of step (i) is/are characterized by a growth rate in process of at least 1.4 $h^{-1}$;

(b) the at least one microorganism strain(s) of step (i) is/are characterized by a nucleic acid content of at least 28%;

(c) the at least one microorganism strain(s) of step (i) comprises a bacterial strain, wherein the bacterial strain is characterized by a genomic G/C content of at least 55%;

(d) the at least one microorganism strain(s) of step (i) comprises a microorganism that is a vitamin B12 autotroph;

(e) step (i) is performed as a continuous process with a dilution rate of at least 1.4 $h^{-1}$, wherein the growth rate in process of each of the at least one microorganism strain(s) of step (i) is limited by the dilution rate, and optionally wherein the at least one microorganism strain(s) is cultivated under non-sterile conditions;

(f) the at least one microorganism strain(s) of step (i) are two bacterial strains; and/or (g) the at least one microorganism strain(s) comprises a microorganism strain selected from *Vibrio natriegens*, *Geobacillus* LC300, and *Bacillus megaterium*.

11. The method according to claim 1, wherein (f) the at least one microorganism strain(s) of step (i) are two bacterial strains, wherein at least one bacterial strain is a vitamin B12 autotroph.

12. The method according to claim 1, wherein (a) step (ii) involves heat pre-treatment performed at a temperature of between 70° C. and 180° C. and/or for a time of between 10 minutes and 360 minutes, followed by enzymatic treatment with protease(s) at a temperature of between 40° C. and 100° C., and/or at a pH of between 3.0 and 9.0, and/or for a time of between 0.5 and 72 hours;

(b) step (ii) is performed by mechanical homogenization, and involves heat pre-treatment performed at a temperature of between 70° C. and 180° C. and/or for a time of between 10 minutes and 360 minutes;

(c) step (iii) involves enzymatic treatment with nuclease (s) at a temperature of between 40° C. and 100° C., and/or at a pH of between 3.0 and 9.0, and/or for a time of between 0.5 and 72 hours;

(d) step (iii) further comprises enzymatic treatment with deaminase(s) at a temperature of between 40° C. and 100° C., and/or at a pH of between 3.0 and 9.0, and/or for a time of between 0.5 and 72 hours; and/or (e) step (iii) further comprises enzymatic treatment with protease(s) at a temperature of between 40° C. and 100° C., and/or at a pH of between 3.0 and 9.0, and/or for a time of between 0.5 and 72 hours.

13. The method according to claim 1, wherein (a) step (ii) involves heat pre-treatment performed at a temperature of between 70° C. and 180° C. and/or for a time of between 10 minutes and 360 minutes, followed by enzymatic treatment with protease(s), at a temperature of between 45° C. and 70° C., and/or at a pH of between 5.0 and 7.0, and/or for a time of between 0.5 and 10 hours;

(b) step (ii) is performed by mechanical homogenization, and optionally involves heat pre-treatment performed at a temperature of between 70° C. and 180° C. and/or for a time of between 10 minutes and 360 minutes;

(c) step (iii) involves enzymatic treatment with nuclease (s) at a temperature of between 45° C. and 70° C., and/or at a pH of between 5.0 and 7.0, and/or for a time of between 0.5 and 10 hours;

(d) step (iii) further comprises enzymatic treatment with deaminase(s) at a temperature of between 45° C. and 70° C., and/or at a pH of between 5.0 and 7.0, and/or for a time of between 0.5 and 10 hours; and/or (e) step (iii) further comprises enzymatic treatment with protease(s) at a temperature of between 45° C. and 70° C., and/or at a pH of between 5.0 and 7.0, and/or for a time of between 0.5 and 10 hours.

14. The composition of claim 5, (a) characterized in IMP/GMP content of at least 17%; and/or (b) further comprising glutamate content of at least 16% w/w.

* * * * *